(12) United States Patent
Kaji

(10) Patent No.: US 12,402,987 B2
(45) Date of Patent: Sep. 2, 2025

(54) DATA PROCESSING APPARATUS, DATA PROCESSING METHOD, AND DATA PROCESSING SYSTEM

(71) Applicant: J. MORITA MFG. CORP., Kyoto (JP)

(72) Inventor: Ryosuke Kaji, Kyoto (JP)

(73) Assignee: J. MORITA MFG. CORP., Kyoto (JP)

( * ) Notice: Subject to any disclaimer, the term of this patent is extended or adjusted under 35 U.S.C. 154(b) by 381 days.

(21) Appl. No.: 18/057,908

(22) Filed: Nov. 22, 2022

(65) Prior Publication Data

US 2023/0218375 A1 Jul. 13, 2023

(30) Foreign Application Priority Data

Dec. 2, 2021 (JP) ................. 2021-196014

(51) Int. Cl.
*A61C 9/00* (2006.01)
*G06T 7/00* (2017.01)
*G06T 7/90* (2017.01)

(52) U.S. Cl.
CPC .......... *A61C 9/0053* (2013.01); *G06T 7/0014* (2013.01); *G06T 7/90* (2017.01);
(Continued)

(58) Field of Classification Search
CPC ....... A61C 9/0053; G06T 7/0014; G06T 7/90; G06T 2207/10024; G06T 2207/30036; G06T 5/50; G06T 2207/10016; G06T 2207/10028; G06T 2207/30168; G06T 7/0002; A61B 5/0088; A61B 5/0062; A61B 2034/105; A61B 2090/3618; A61B 2090/364; A61B 2090/373; A61B 90/361
(Continued)

(56) References Cited

U.S. PATENT DOCUMENTS 6,512,994 B1 * 1/2003 Sachdeva ............... A61C 7/146
702/167
10,219,875 B1 3/2019 Kopelman et al.
(Continued)

FOREIGN PATENT DOCUMENTS

JP 2009-523552 A 6/2009
JP 2014-521163 A 8/2014
(Continued)

OTHER PUBLICATIONS

Office Action issued Apr. 2, 2024, in corresponding Japanese Patent Application No. 2021-196014 (with English Translation), 12 pages.
(Continued)

*Primary Examiner* — Ali Bayat
(74) *Attorney, Agent, or Firm* — Oblon, McClelland, Maier & Neustadt, L.L.P.

(57) ABSTRACT

The data processing apparatus includes a scanner interface to which three-dimensional data acquired by the three-dimensional scanner is inputted, and processing circuitry configured to verify first three-dimensional data input from the scanner interface and second three-dimensional data input from the scanner interface by comparing the first three-dimensional data and the second three-dimensional data in a virtual space set with respect to the position of the three-dimensional scanner.

10 Claims, 16 Drawing Sheets

(52) U.S. Cl.
CPC ............... *G06T 2207/10024* (2013.01); *G06T 2207/30036* (2013.01)

(58) Field of Classification Search
USPC ........................................................ 382/154
See application file for complete search history.

(56) References Cited

U.S. PATENT DOCUMENTS

| | | | |
|---|---|---|---|
| 12,062,170 B2* | 8/2024 | Ezhov | ................... G06T 7/0012 |
| 2009/0316966 A1 | 12/2009 | Marshall et al. | |
| 2014/0212832 A1* | 7/2014 | Fisker | ................... A61B 5/0062 |
| | | | 433/29 |
| 2016/0256035 A1 | 9/2016 | Kopelman et al. | |
| 2016/0331493 A1 | 11/2016 | Kopelman et al. | |
| 2017/0156824 A1* | 6/2017 | Rubbert | ................... A61L 27/16 |
| 2018/0025529 A1* | 1/2018 | Wu | ........................ G01J 3/501 |
| | | | 345/426 |
| 2018/0049641 A1 | 2/2018 | Fisker et al. | |
| 2018/0271619 A1 | 9/2018 | Kopelman et al. | |
| 2018/0360317 A1 | 12/2018 | Fisker et al. | |
| 2019/0290398 A1 | 9/2019 | Kopelman et al. | |
| 2020/0170760 A1 | 6/2020 | Dawood | |
| 2020/0197129 A1 | 6/2020 | Kopelman et al. | |
| 2020/0265653 A1 | 8/2020 | Hawkins et al. | |
| 2021/0217189 A1 | 7/2021 | Sorimoto et al. | |
| 2022/0157034 A1 | 5/2022 | Hawkins et al. | |
| 2023/0021695 A1* | 1/2023 | Atiya | ................. A61B 1/00194 |
| 2023/0218374 A1 | 7/2023 | Kaji | |

FOREIGN PATENT DOCUMENTS

| | | |
|---|---|---|
| JP | 2021-58672 A | 4/2021 |
| JP | 2021-111254 A | 8/2021 |
| JP | 2021-117051 A | 8/2021 |
| JP | 2023-82326 A | 6/2023 |
| WO | WO 2007/084647 A2 | 7/2007 |
| WO | WO 2018/219800 A1 | 12/2018 |
| WO | WO 2020/1855271 A1 | 9/2020 |
| WO | WO 2023/014107 A | 2/2023 |

OTHER PUBLICATIONS

Kokura et al., "Examination of the method for dividing a three dimensional point group consisting of a plurality of three dimensional objects", Multimedia, Dispersion, Cooperative and Mobile (DICOMO2018) Symposium Paper Collection [CD-ROM], Information Processing Society, 2018, pp. 236-246.

Extended European Search Report issued May 10, 2023 in European Application No. 22209328.8, 10 pages.

* cited by examiner

FIG.10

THREE-DIMENSIONAL DATA TABLE

| DATA TYPE | POSITION INFORMATION | | | COLOR INFORMATION | DELETION FLAG |
|---|---|---|---|---|---|
| | X | Y | Z | | |
| DATA 1 | X1 | Y1 | Z1 | C1 | 0 |
| DATA 2 | X2 | Y2 | Z2 | C2 | 0 |
| DATA 3 | X3 | Y3 | Z3 | C3 | 0 |
| DATA 4 | X4 | Y4 | Z4 | C4 | 0 |
| DATA 5 | X5 | Y5 | Z5 | C5 | 0 |
| ⋮ | ⋮ | ⋮ | ⋮ | ⋮ | ⋮ |
| DATA n1 | Xn1 | Yn1 | Zn1 | Cn1 | 1 |
| DATA n2 | Xn2 | Yn2 | Zn2 | Cn2 | 1 |
| DATA n3 | Xn3 | Yn3 | Zn3 | Cn3 | 1 |
| DATA n4 | Xn4 | Yn4 | Zn4 | Cn4 | 0 |
| DATA n5 | Xn5 | Yn5 | Zn5 | Cn5 | 0 |
| ⋮ | ⋮ | ⋮ | ⋮ | ⋮ | ⋮ |

FIG.12

DATA SET TABLE

| DATA SET TYPE | NUMBER OF MESHES |
|---|---|
| DATA SET 1 | 114590 |
| DATA SET 2 | 17209 |
| DATA SET 3 | 15 |
| DATA SET 4 | 6 |
| DATA SET 5 | 2 |
| ⋮ | ⋮ |

DATA PROCESSING APPARATUS, DATA PROCESSING METHOD, AND DATA PROCESSING SYSTEM

BACKGROUND OF THE DISCLOSURE

Field of the Disclosure

The present disclosure relates to a data processing apparatus, a data processing method, and a data processing system that process three-dimensional data including the position of each point of a point group representing at least the surface of an object, the three-dimensional data being acquired by a three-dimensional scanner.

Description of the Background Art

Conventionally, in the field of dentistry, a technique of acquiring three-dimensional data on objects such as teeth by scanning an oral cavity with a three-dimensional scanner has been known. During a scan with a three-dimensional scanner, an operator's finger, a dental instrument, or obstacles such as the tongue of a patient may enter between the three-dimensional scanner and objects such as teeth to be scanned. This may prevent the three-dimensional scanner from properly acquiring three-dimensional data on an object to be scanned. In this respect, Japanese Patent Publication No. 2021-111254 discloses an information processing device capable of deleting three-dimensional data selected by a user from three-dimensional data acquired by a three-dimensional scanner.

SUMMARY

According to the information processing device disclosed in Japanese Patent Publication No. 2021-111254, the user can correct the three-dimensional data acquired by the three-dimensional scanner even if an obstacle enters an oral cavity during a scan. However, in order to correct the three-dimensional data, the user needs to select three-dimensional data to be deleted from the three-dimensional data acquired by the three-dimensional scanner, requiring a lot of time and effort.

An object of the present disclosure, which has been made to solve the problem, is to provide a technique with which three-dimensional data on an object can be acquired easily and properly by using a three-dimensional scanner.

According to an example of the present disclosure, a data processing apparatus is provided to process three-dimensional data including the position of each point of a point group representing at least the surface of an object, the three-dimensional data being acquired by a three-dimensional scanner. The data processing apparatus includes a scanner interface to which three-dimensional data acquired by the three-dimensional scanner is inputted, and processing circuitry that performs first data processing in which first three-dimensional data inputted from the scanner interface and second three-dimensional data inputted from the scanner interface are verified by comparing the first three-dimensional data and the second three-dimensional data in a virtual space set with respect to the position of the three-dimensional scanner.

According to an example of the present disclosure, a data processing method is provided to cause a computer to process three-dimensional data including the position of each point of a point group representing at least an object surface, the three-dimensional data being acquired by a three-dimensional scanner. As processing to be performed by the computer, the data processing method includes: receiving the three-dimensional data acquired by the three-dimensional scanner; and performing first data processing in which first three-dimensional data received by the receiving and second three-dimensional data received by the receiving are verified by comparing the first three-dimensional data and the second three-dimensional data in a virtual space set with respect to the position of the three-dimensional scanner.

According to an example of the present disclosure, a data processing system is provided. The data processing system includes a three-dimensional scanner that acquires three-dimensional data including the position of each point of a point group representing at least the surface of an object by scanning an object in an oral cavity and a data processing apparatus that processes the three-dimensional data acquired by the three-dimensional scanner. The data processing apparatus includes a scanner interface to which three-dimensional data acquired by the three-dimensional scanner is inputted, and processing circuitry that performs first data processing in which first three-dimensional data inputted from the scanner interface and second three-dimensional data inputted from the scanner interface are verified by comparing the first three-dimensional data and the second three-dimensional data in a virtual space set with respect to the position of the three-dimensional scanner.

The foregoing and other objects, features, aspects and advantages of the present disclosure will become more apparent from the following detailed description of the present disclosure when taken in conjunction with the accompanying drawings.

BRIEF DESCRIPTION OF THE DRAWINGS

FIG. 10 shows an example of a three-dimensional data table;

FIG. 12 shows an example of a data set table;

DETAILED DESCRIPTION

Figure 1:
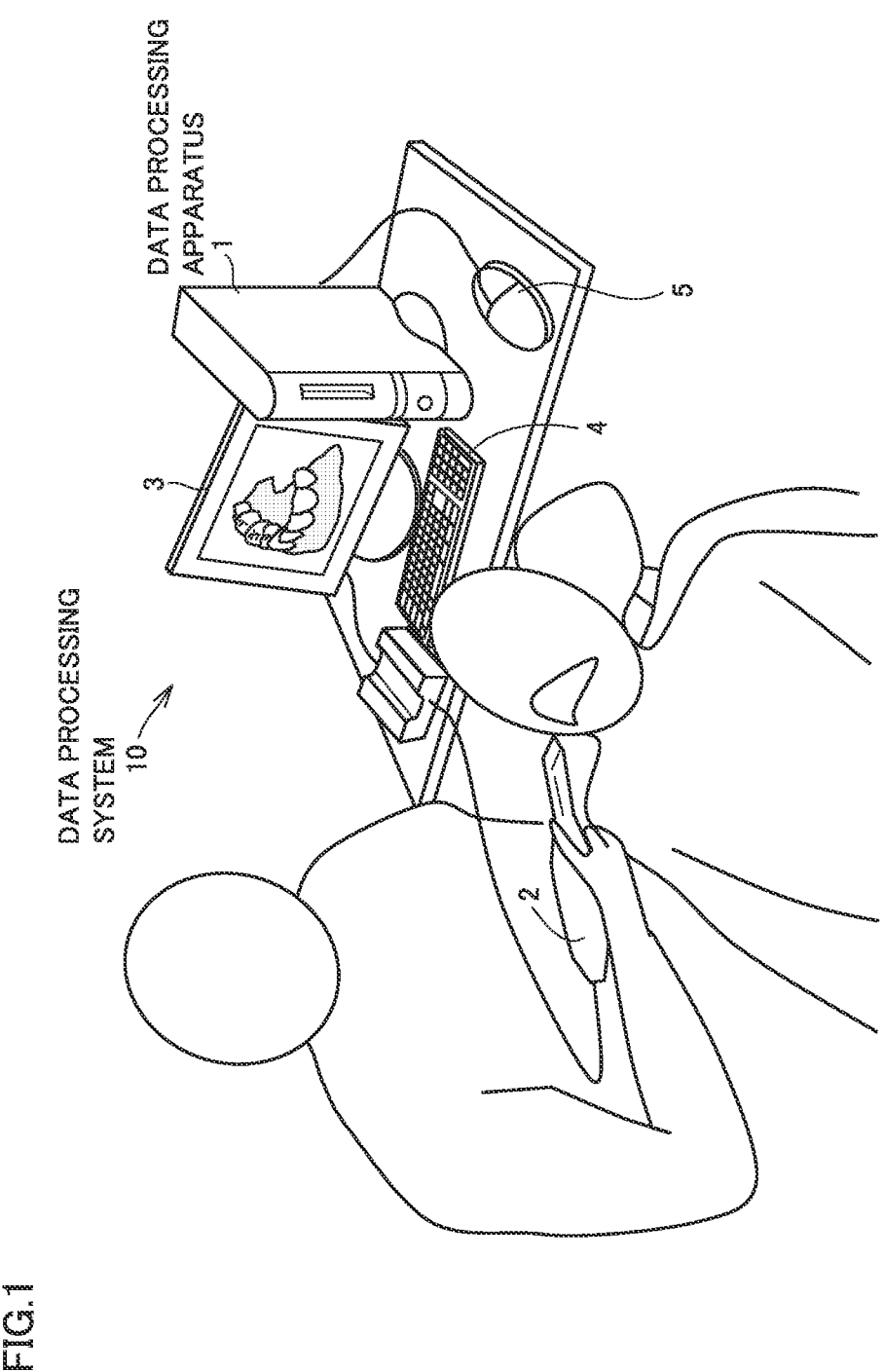
FIG. 1 illustrates an application example of a data processing system and a data processing apparatus according to the present embodiment.

An embodiment according to the present disclosure will be specifically described below with reference to the accompanying drawings. The same parts or equivalent parts in the drawings are indicated by the same reference numerals and a repetition of a description thereof is omitted.

Application Example

Referring to FIG. 1, an application example of a data processing system 10 and a data processing apparatus 1 according to the present embodiment will be described below. FIG. 1 illustrates the application example of data processing system 10 and data processing apparatus 1 according to the present embodiment.

As illustrated in FIG. 1, a user can acquire three-dimensional data on an object in the oral cavity of a subject by scanning the oral cavity with a three-dimensional scanner 2. "User" may be any user, e.g., an operator like a dentist, a dental nurse, a doctor or a student at a dental college, a dental mechanic, an engineer from a manufacturer, or an operator at a manufacturing site if the user acquires three-dimensional data on objects such as teeth with three-dimensional scanner 2. "Subject" may be any subject, e.g., a patient at a dental clinic or a test subject at a dental college if the subject can be scanned with three-dimensional scanner 2. "Object" may be any object, e.g., teeth in the oral cavity of a subject if the object can be scanned with three-dimensional scanner 2. Hereinafter, an object to be scanned will be also referred to as "scan object."

Data processing system 10 includes data processing apparatus 1 and three-dimensional scanner 2. A display 3, a keyboard 4, and a mouse 5 are connected to data processing apparatus 1.

Three-dimensional scanner 2 acquires three-dimensional data on a scan object by using a built-in three-dimensional camera. Specifically, by scanning an oral cavity, three-dimensional scanner 2 acquires three-dimensional data on the position (the coordinates in axes in vertical, horizontal, and height directions) of each point of a point group representing the surface of the scan object through an optical sensor or the like. In other words, the three-dimensional data includes position information on the position (the coordinates in axes in vertical, horizontal, and height directions) of each point of the point group constituting the surface of the scan object.

Since the range of measurement by three-dimensional scanner 2 is limited, the user who requires three-dimensional data on a row of teeth (dental arch) in an oral cavity scans the oral cavity several times while moving three-dimensional scanner 2 along the row of teeth in the oral cavity.

Data processing apparatus 1 generates two-dimensional image data, which corresponds to a two-dimensional image viewed from any viewpoint, on the basis of the three-dimensional data acquired by the three-dimensional scanner 2 and displays the two-dimensional image corresponding to the generated two-dimensional image data on display 3, allowing the user to view a two-dimensional projection drawing of the surface of a scan object in a specific direction.

Moreover, data processing apparatus 1 outputs the three-dimensional data to a dental laboratory. In the dental laboratory, a dental technician fabricates tooth models such as prostheses on the basis of the three-dimensional data acquired from data processing apparatus 1. If a machine capable of automatically fabricating tooth models, for example, a milling machine or a 3D printer is disposed in a dental clinic, data processing apparatus 1 may output the three-dimensional data to the automatic fabricating machine.

[Hardware Configuration of Data Processing Apparatus]

Figure 2:
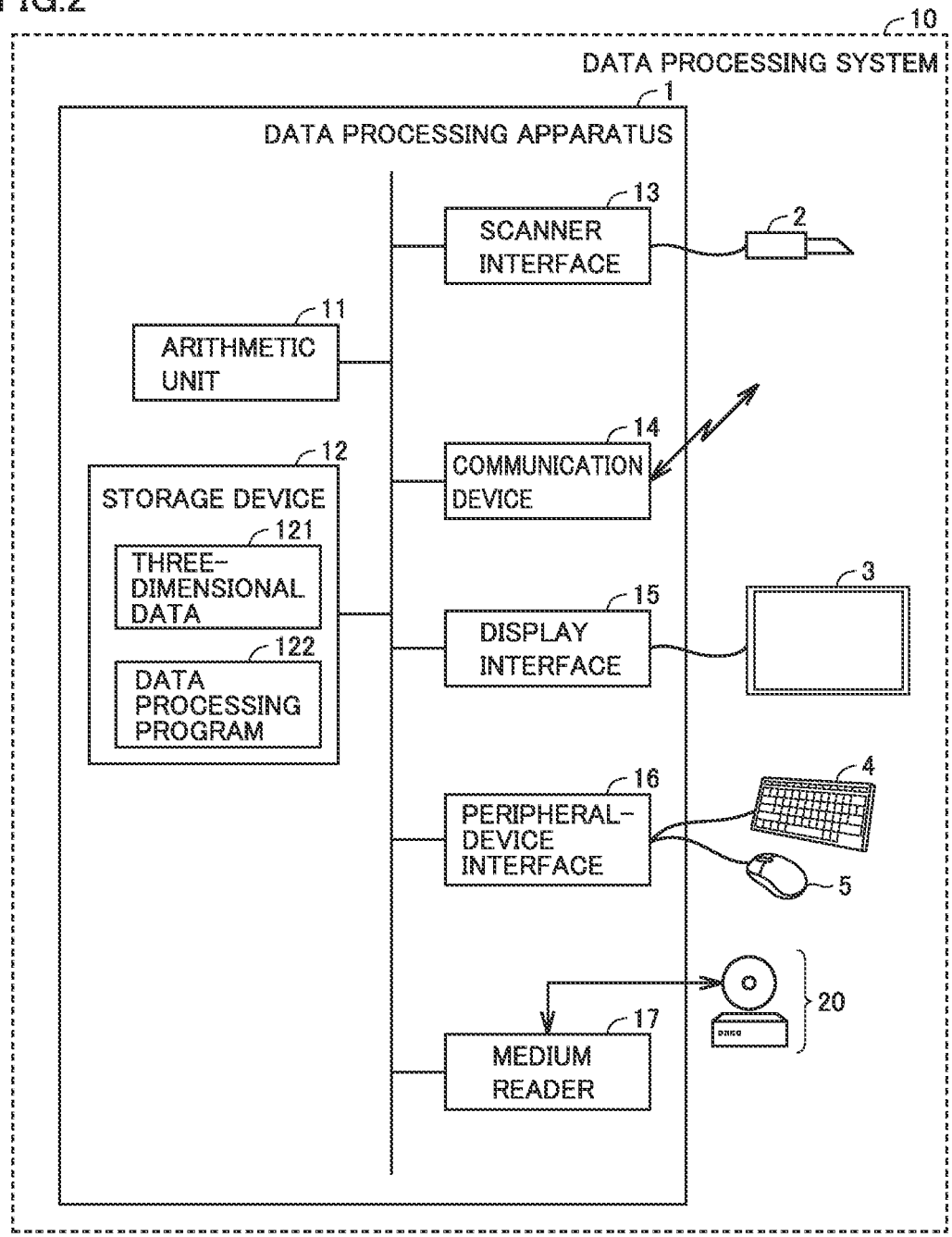
FIG. 2 is a block diagram illustrating the hardware configuration of the data processing apparatus according to the present embodiment.

Referring to FIG. 2, the hardware configuration of data processing apparatus 1 according to the present embodiment will be described below. FIG. 2 is a block diagram illustrating the hardware configuration of data processing apparatus 1 according to the present embodiment. Data processing apparatus 1 may be implemented by a general-purpose computer or a computer specific for data processing system 10.

As illustrated in FIG. 2, data processing apparatus 1 includes, as main hardware elements, an arithmetic unit 11, a storage device 12, a scanner interface 13, a communication device 14, a display interface 15, a peripheral-device interface 16, and a medium reader 17.

Arithmetic unit 11 is an arithmetic main unit that performs various kinds of processing by executing various programs and is an example of computers such as a processor. Arithmetic unit 11 (processor) includes, for example, a microcontroller, a CPU (central processing unit), or an MPU (Micro-processing unit). A processor has the functions of performing various kinds of processing by executing programs. Some or all of the functions may be implemented by using dedicated hardware circuits such as an ASIC (Application Specific Integrated Circuit) or an FPGA (Field-Programmable Gate Array). "Processor" is not strictly limited to a processor that performs processing according to a stored program method like a CPU or an MPU, and may include hard wired circuits such as an ASIC or an FPGA. Thus, a processor can be also read as processing circuitry in which processing is defined in advance by a computer-readable code and/or a hard wired circuit. The processor may include a single chip or a plurality of chips. Furthermore, the processor and related processing circuits may include a plurality of computers making wired or wireless connection via a local area network or a wireless network. The processor and related processing circuits may include cloud computers that perform remote operations based on input data and output the operation results to other devices at remote locations. Arithmetic unit 11 may include at least one of a CPU, an FPGA, and a GPU or may include a CPU and an FPGA, an FPGA and a GPU, a CPU and a GPU, or all of a CPU, an FPGA, and a GPU.

Storage device 12 includes a volatile storage area (e.g., a working area) for temporarily storing a program code or a work memory when arithmetic unit 11 executes any program. Storage device 12 may be one or more non-transitory computer readable media. For example, storage device 12 includes volatile memory devices such as a DRAM (Dynamic Random Access Memory) or an SRAM (Static Random Access Memory). Furthermore, storage device 12 includes a nonvolatile storage area. Storage device 12 may be one or more computer readable storage media. For example, storage device 12 includes ROM (Read Only Memory), a hard disk, or nonvolatile memory devices such as an SSD (Solid State Drive).

The present embodiment described an example in which a volatile storage area and a nonvolatile storage area are included in the same storage device 12. A volatile storage area and a nonvolatile storage area may be included in different storage devices. For example, arithmetic unit 11 may include a volatile storage area, whereas storage device 12 may include a nonvolatile storage area. Data processing apparatus 1 may be provided with a microcomputer including arithmetic unit 11 and storage device 12.

Storage device 12 stores three-dimensional data 121 acquired by three-dimensional scanner 2 and a data processing program 122. Data processing program 122 is a program for causing arithmetic unit 11 to perform data processing (processing in FIG. 13, which will be described later) on the three-dimensional data acquired from three-dimensional scanner 2.

Scanner interface 13 is an interface for connecting three-dimensional scanner 2 and provides data input/output between data processing apparatus 1 and three-dimensional scanner 2. Data processing apparatus 1 and three-dimensional scanner 2 make a wired connection via a cable or a wireless connection (WIFI, BLUETOOTH, and the like).

Communication device 14 transmits and receives data to and from the dental laboratory or the automatic fabricating machine through wire communications or radio communications. For example, data processing apparatus 1 transmits the three-dimensional data to the dental laboratory or the automatic fabricating machine through communication device 14.

Display interface 15 is an interface for connecting display 3 and provides data input/output between data processing apparatus 1 and display 3.

Peripheral-device interface 16 is an interface for connecting peripheral devices such as keyboard 4 and mouse 5 and provides data input/output between data processing apparatus 1 and the peripheral devices.

Medium reader 17 reads various kinds of data stored in a removable disk 20 that is a storage medium. The storage medium illustrated as removable disk 20 is a non-transitory and tangible computer readable storage medium and may be provided in any forms such as a CD (Compact Disc), a DVD (Digital Versatile Disc), or USB (Universal Serial Bus) memory if various kinds of data can be recorded. For example, medium reader 17 may acquire data processing program 122 from removable disk 20.

[Configuration of Three-Dimensional Scanner]

Figure 3:
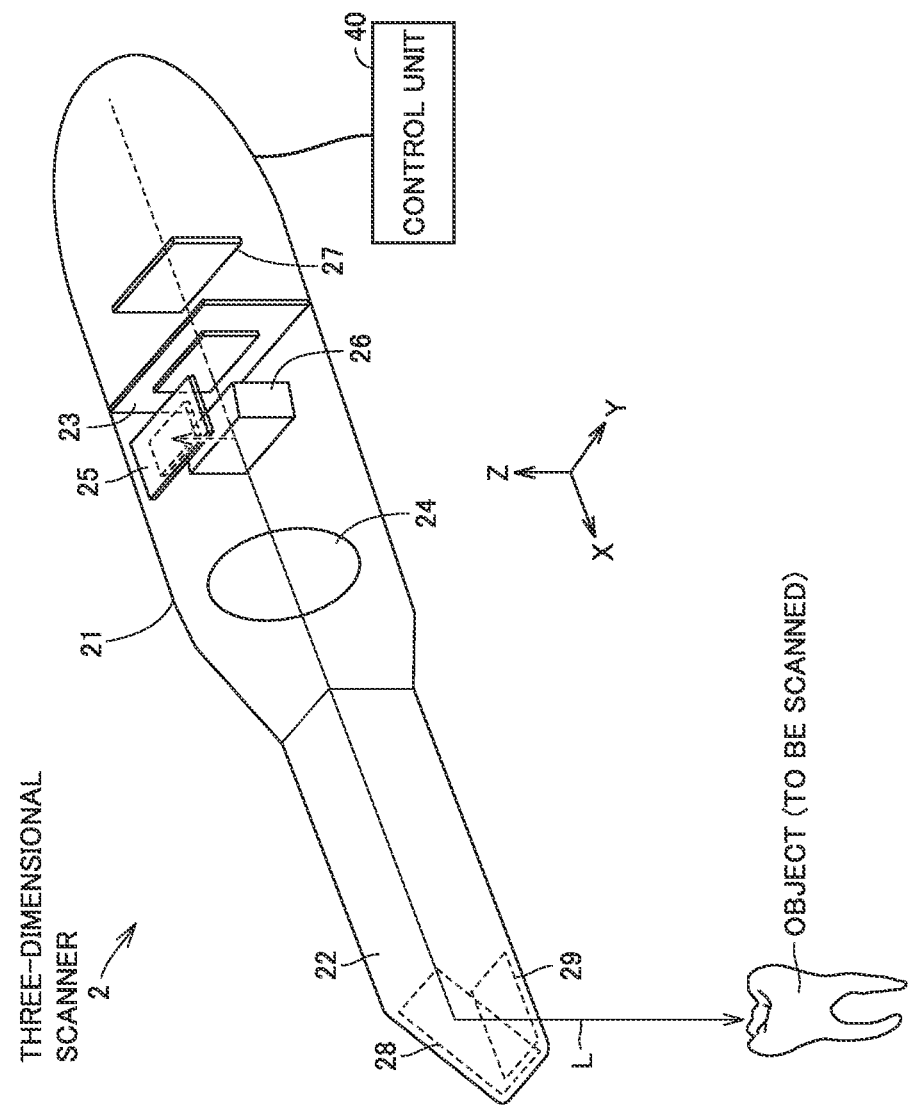
FIG. 3 illustrates the configuration of a three-dimensional scanner according to the present embodiment.

Referring to FIG. 3, the configuration of three-dimensional scanner 2 according to the present embodiment will be described below. FIG. 3 illustrates the configuration of three-dimensional scanner 2 according to the present embodiment.

As illustrated in FIG. 3, three-dimensional scanner 2 is a hand-held handpiece including a housing 21, a probe 22 detachably connected to housing 21, and a control unit 40.

Probe 22 is inserted into an oral cavity and projects patterned light (hereinafter also simply referred to as "pattern") onto a scan object. Probe 22 guides light reflected with a projected pattern from the scan object into housing 21.

Three-dimensional scanner 2 includes a light source 23, a lens 24, an optical sensor 25, a prism 26, and a counterweight 27 in housing 21. In FIG. 3, for convenience of explanation, a direction along which lens 24 and counterweight 27 make reciprocating motions is denoted as the X axis, an axis that is perpendicular to the X axis and is directed upward in FIG. 3 is denoted as the Z axis, and an axis perpendicular to the X axis and Z axis is denoted as the Y axis.

Light source 23 includes a laser element or an LED (Light Emitting Diode). Light (optical axis L) from light source 23 passes through prism 26 and lens 24, is reflected by a reflecting part 28 provided for probe 22, and is outputted from an opening 29. The light outputted from opening 29 is directed onto a scan object and is reflected by the scan object. The light reflected by the scan object enters housing 21 again through opening 29 and reflecting part 28 and is inputted into prism 26 through lens 24. Prism 26 changes the traveling direction of light from an object to a direction in which optical sensor 25 is located (the Z-axis direction in this example). After the traveling direction of light is changed by prism 26, the light is detected by optical sensor 25.

If three-dimensional data on an object is acquired by using a focusing technique, light passing through a pattern generating element (not illustrated) provided between lens 24 and the object is projected to the object. A reciprocating motion by lens 24 on the same straight line (e.g., the X axis) changes the focusing position of a projection pattern. Optical sensor 25 detects light from the scan object each time the focusing position is changed.

Control unit 40 includes, for example, a CPU, ROM, and RAM and controls processing performed in three-dimensional scanner 2. Control unit 40 may include an FPGA or a GPU. In one embodiment, control unit 40 may include at least one of a CPU, an FPGA, and a GPU or may include a CPU and an FPGA, an FPGA and a GPU, a CPU and a GPU, or all of a CPU, an FPGA, and a GPU. Control unit 40 may include processing circuitry.

Control unit 40 calculates the positions of points representing the surface of the scan object on the basis of the position of lens 24 and the detection result of optical sensor 25 at that time. Object three-dimensional data acquired thus by three-dimensional scanner 2 is inputted to data processing apparatus 1 through scanner interface 13. Data processing apparatus 1 may have some or all of the functions of control unit 40. For example, arithmetic unit 11 of data processing apparatus 1 may have the functions of control unit 40.

[Example of Scan by Three-Dimensional Scanner]

Figure 4:
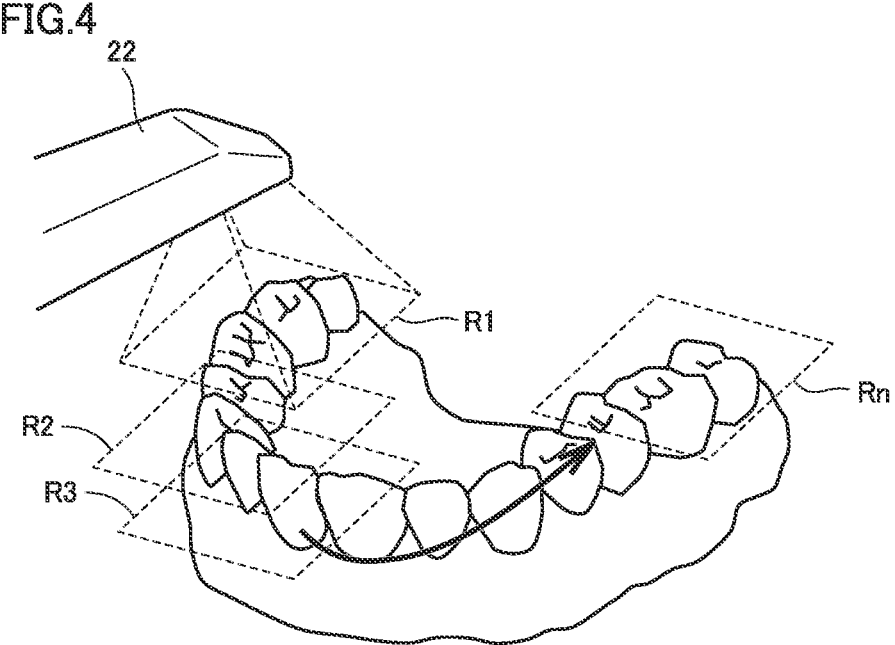
FIG. 4 is an explanatory drawing of a scanning method by the three-dimensional scanner.
Figure 5:
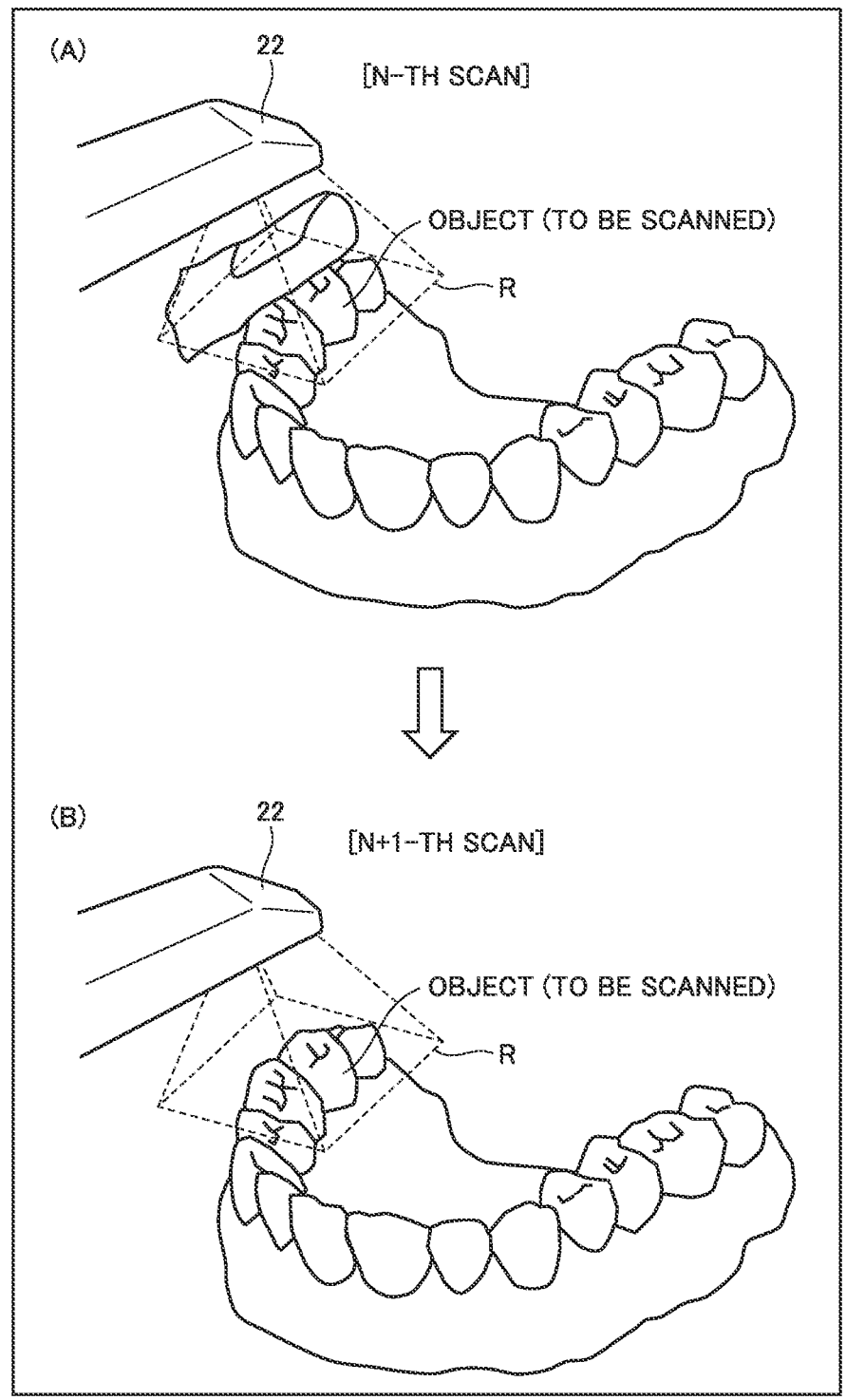
FIG. 5 illustrates an example of a scan performed by the three-dimensional scanner.

Referring to FIGS. 4 and 5, an example of a scan by three-dimensional scanner 2 will be described below. FIG. 4 is an explanatory drawing of a scanning method by three-dimensional scanner 2.

The scanning range of three-dimensional scanner 2 is limited by the size of probe 22 insertable into an oral cavity. Thus, a user inserts probe 22 into the oral cavity and then scans the oral cavity several times while moving probe 22 along a row of teeth in the oral cavity.

For example, as illustrated in FIG. 4, the user acquires three-dimensional data at various positions in an oral cavity by moving probe 22 sequentially in scan ranges R1, R2, R3, . . . , and Rn in the oral cavity. In this way, the user scans a scan object while moving probe 22, allowing three-dimensional scanner 2 to acquire three-dimensional data on the scan object. In scan ranges R1 to Rn of FIG. 4, the user scans from the occlusal surface of a molar or an incisor but may scan from a lingual surface or a buccal surface. Thus, the user can more securely acquire three-dimensional data on teeth by using three-dimensional scanner 2.

FIG. 5 illustrates an example of a scan performed by three-dimensional scanner 2. During a scan with three-dimensional scanner 2, an operator's finger, a dental instrument, or obstacles such as the tongue of a patient may enter between a scan object and probe 22. This may prevent three-dimensional scanner 2 from properly acquiring three-dimensional data on the scan object.

For example, in the example of FIG. 5(A), an operator's finger (e.g., a user's finger) is placed in scan range R of three-dimensional scanner 2 during the N-th scan. In this case, as illustrated in FIG. 5(B), the user removes obstacles such as a finger and then scans the scan object again at the same place in the subsequent N+1-th scan.

In the foregoing example, the user acquires three-dimensional data in the N+1-th scan as true data but needs to process three-dimensional data in the N-th scan as false data. Thus, data processing apparatus 1 according to the present embodiment is configured to verify whether three-dimensional data in the N-th scan and three-dimensional data in the N+1-th scan are true or not by comparing the three-dimensional data in the N-th scan and the three-dimensional data in the N+1-th scan, the three-dimensional data being inputted from three-dimensional scanner 2. The data verification of data processing apparatus 1 will be specifically described below.

[Functional Configuration of Data Processing Apparatus]

Figure 6:
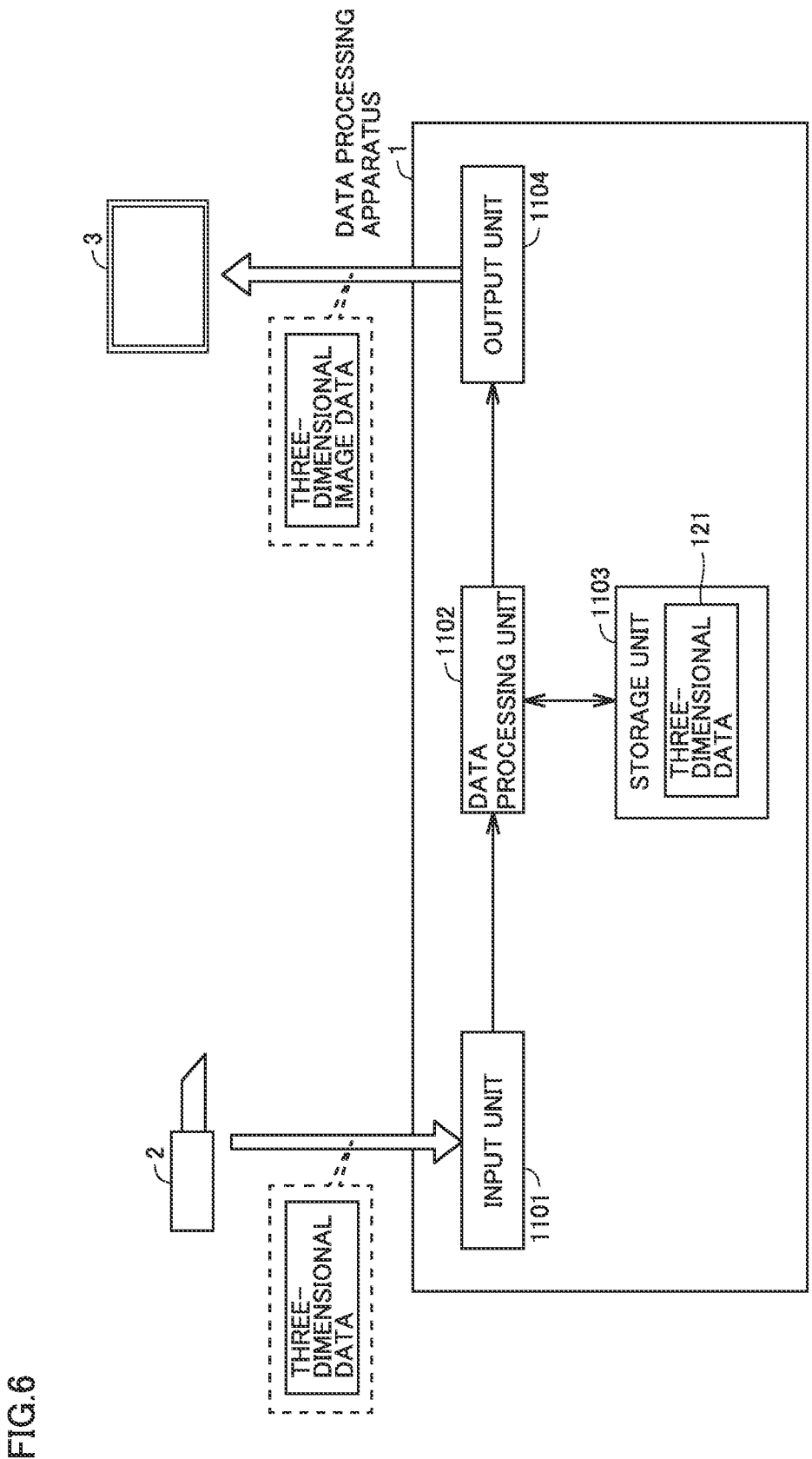
FIG. 6 is a block diagram illustrating the functional configuration of the data processing apparatus according to the present embodiment.

Referring to FIG. 6, the functional configuration of data processing apparatus 1 according to the present embodiment will be described below. FIG. 6 is a block diagram illustrating the functional configuration of data processing apparatus 1 according to the present embodiment.

As illustrated in FIG. 6, data processing apparatus 1 includes, as main functional parts, an input unit 1101, a data processing unit 1102, a storage unit 1103, and an output unit 1104.

Input unit 1101 is the functional part of scanner interface 13. Three-dimensional data acquired by three-dimensional scanner 2 is inputted to input unit 1101.

Input unit 1101 may serve as the functional part of communication device 14, peripheral-device interface 16, or medium reader 17. For example, if input unit 1101 is the functional part of communication device 14, communication device 14 acquires three-dimensional data from an external device through wire communications or radio communications. The external device may be a server installed in a dental clinic or a cloud server installed at a location different from a dental clinic. If input unit 1101 is the functional part of peripheral-device interface 16, peripheral-device interface 16 acquires three-dimensional data inputted by a user with keyboard 4 and mouse 5. If input unit 1101 is the functional part of medium reader 17, medium reader 17 acquires three-dimensional data stored in removable disk 20.

Data processing unit 1102 is the functional part of arithmetic unit 11. Data processing unit 1102 performs mesh generation for generating sets of three-dimensional data (hereinafter also referred to as "data sets") by using three-dimensional data 121 that is inputted from input unit 1101 and is accumulated and stored in storage unit 1103. Data processing unit 1102 performs data verification for verifying whether a data set is true or not. If a plurality of data sets are generated by three-dimensional data that is set as true three-dimensional data, data processing unit 1102 performs data set verification in which the data set with the largest data amount among the plurality of data sets is set as a true data set. Furthermore, data processing unit 1102 performs image data generation for generating, on the basis of the true data set, two-dimensional image data corresponding to a two-dimensional image viewed from any viewpoint. Data processing unit 1102 outputs the generated two-dimensional image data to output unit 1104.

Output unit 1104 is the functional part of display interface 15 and outputs the two-dimensional image data generated by data processing unit 1102 to display 3. Thus, data processing apparatus 1 can display a two-dimensional image, which represents the surface shape of a scan object, on display 3.

Output unit 1104 may serve as the functional part of communication device 14 or medium reader 17. For example, if output unit 1104 is the functional part of communication device 14, communication device 14 outputs three-dimensional data to a dental laboratory or an automatic fabricating machine through wire communications or radio communications. If output unit 1104 is the functional part of medium reader 17, medium reader 17 outputs three-dimensional data to removable disk 20.

[Data Determination]

Figure 7:
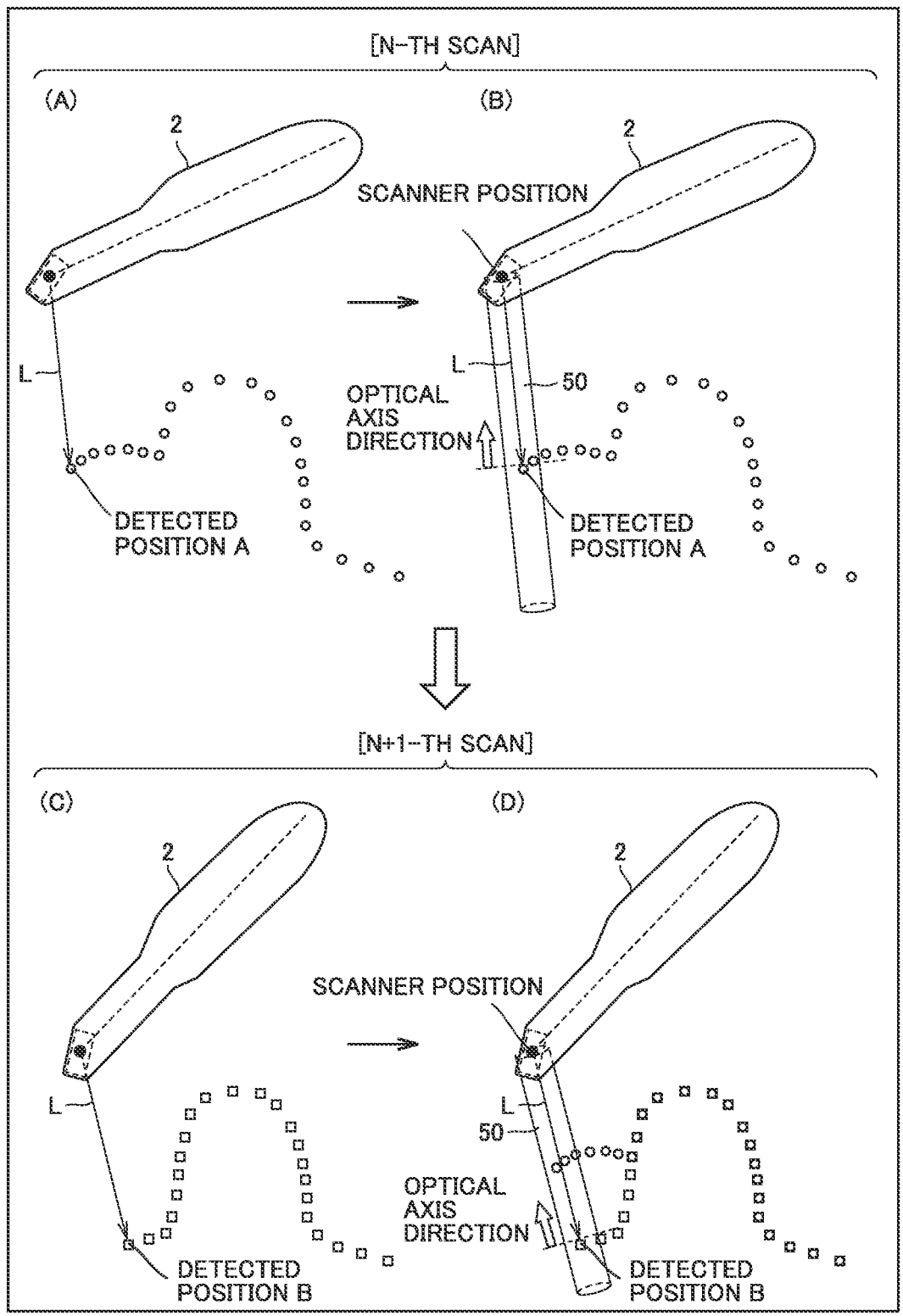
FIG. 7 illustrates an example of the data verification of the data processing apparatus according to the present embodiment.
Figure 8:
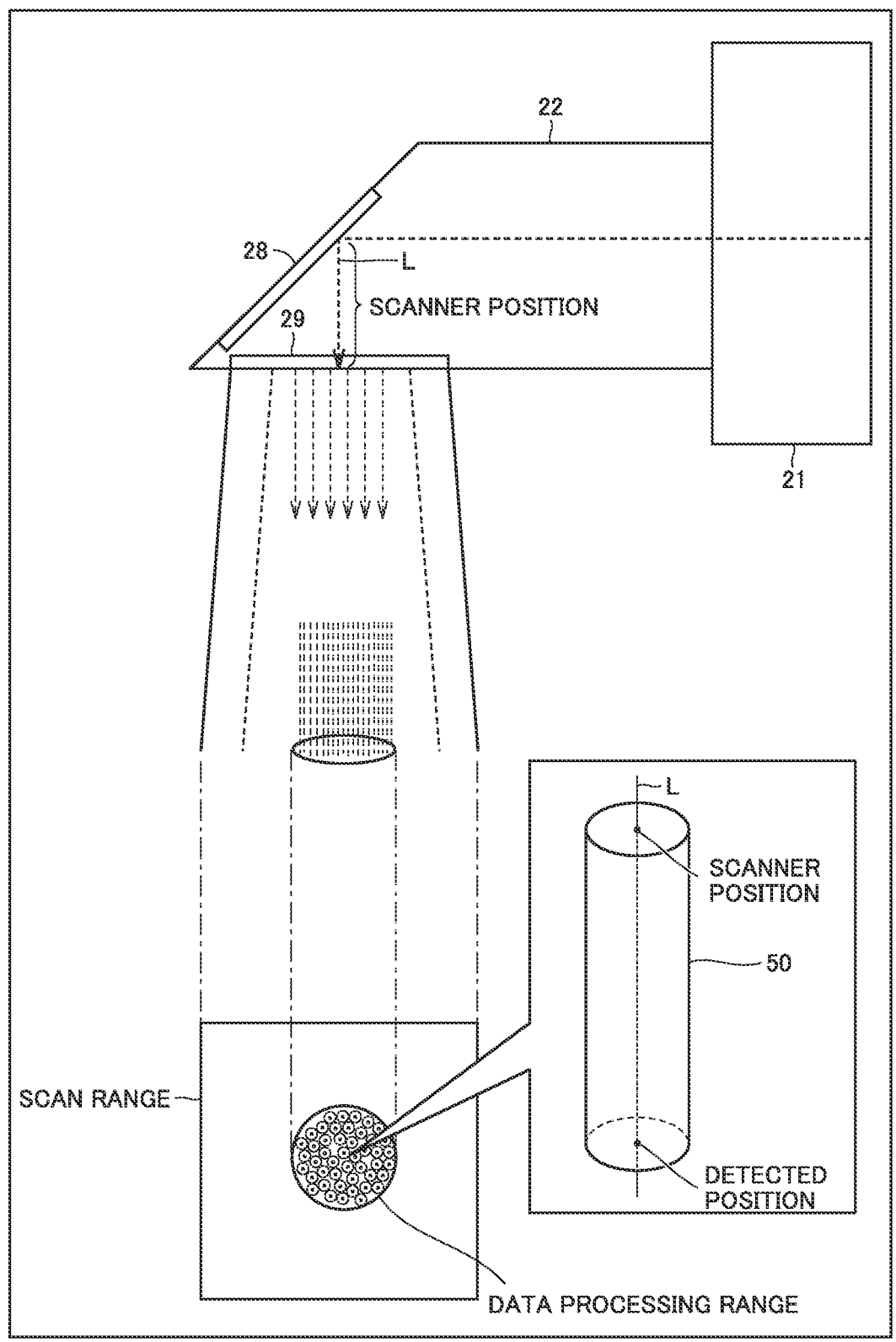
FIG. 8 illustrates an example of the data verification of the data processing apparatus according to the present embodiment.
Figure 9:
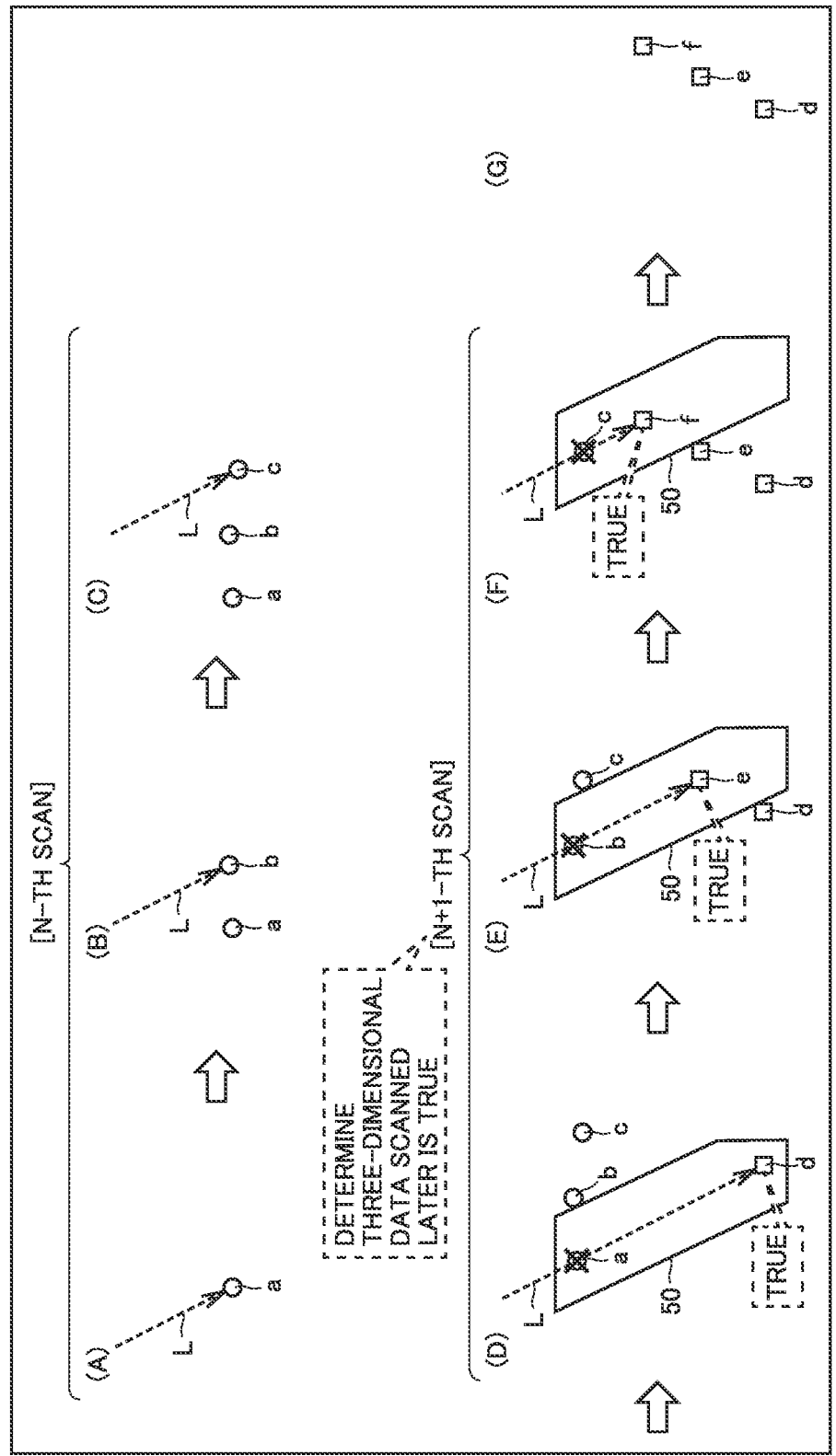
FIG. 9 illustrates an example of the data verification of the data processing apparatus according to the present embodiment.

Referring to FIGS. 7 to 9, the data verification of data processing apparatus 1 according to the present embodiment will be described below. FIGS. 7 to 9 illustrate an example of the data verification of data processing apparatus 1 according to the present embodiment.

By performing the data verification, data processing unit 1102 of data processing apparatus 1 verifies first three-dimensional data inputted from input unit 1101 and second three-dimensional data inputted from input unit 1101, by comparing the first three-dimensional data and the second three-dimensional data in a virtual space 50 set with respect to the position of three-dimensional scanner 2.

For example, as illustrated in FIG. 7, three-dimensional scanner 2 in the N-th scan acquires pieces of three-dimensional data including the positions of a plurality of points representing the surface of a scan object.

When pieces of three-dimensional data are sequentially inputted from three-dimensional scanner 2, data processing apparatus 1 generates virtual space 50 on the basis of the positions of points included in the inputted three-dimensional data and the position of three-dimensional scanner 2.

Referring to FIG. 8, virtual space 50 will be specifically described below. As illustrated in FIG. 8, light (optical axis L) passing through housing 21 from light source 23 is reflected by reflecting part 28 and is outputted to be diffused from opening 29. The light outputted to be diffused with a fixed amount from opening 29 is reflected by the scan object and is directed into housing 21 again through opening 29, so that three-dimensional data is acquired. Thus, the range of a plurality of beams outputted to be diffused from opening 29 serves as a scan range. Data processing apparatus 1 sets a predetermined data processing range in the scan range and generates virtual space 50 on the basis of optical axis L of light included in the data processing range in the light outputted to be diffused with a fixed amount from opening 29.

Specifically, data processing apparatus 1 generates cylindrical virtual space 50 with the central axis located on optical axis L of three-dimensional scanner 2. More specifically, data processing apparatus 1 generates cylindrical virtual space 50 having a predetermined diameter in cross section with the central axis located at optical axis L outputted from opening 29, that is, optical axis L passing through the position of three-dimensional scanner 2 and the position of a point detected by three-dimensional scanner 2 (hereinafter also referred to as "detected position"). Furthermore, if a data processing range includes a plurality of optical axes L, data processing apparatus 1 generates a plurality of cylindrical virtual spaces 50 with the central axes located on respective optical axes L.

In the example of FIG. 8, "the position of the three-dimensional scanner" (hereinafter also referred to as "scanner position") is set at any one of positions on a path where optical axis L having passed through housing 21 from light source 23 is reflected by reflecting part 28 and is outputted through opening 29. The scanner position may be set at any position in three-dimensional scanner 2 if data processing apparatus 1 can recognize a distance from a detected position.

Referring to FIG. 7 again, when a position A of a point is detected in the N-th scan as illustrated in FIG. 7(A), data processing apparatus 1 generates cylindrical virtual space 50 with the central axis located on optical axis L passing through detected position A as illustrated in FIG. 7(B). When virtual space 50 is generated for three-dimensional data (three-dimensional data including position information on detected position A) acquired in the N-th scan, data processing apparatus 1 determines whether three-dimensional data acquired before the N-th scan (for example, in the N−1-th scan in the past) is present in virtual space 50. N is a natural number.

When determining whether three-dimensional acquired in the past is present in virtual space 50, data processing apparatus 1 determines whether three-dimensional data acquired in the past is present in the direction of optical axis L to the scanner position from a point corresponding to detected position A serving as a reference position for generating virtual space 50.

In the example of FIG. 7(B), three-dimensional data acquired before the N-th scan (in the N−1-th scan) is not present in virtual space 50 for the three-dimensional data acquired in the N-th scan. Thus, data processing apparatus 1 determines that the three-dimensional data on detected position A is true three-dimensional data.

Subsequently, in a scan subsequent to the N-th scan (for example, in the N+1 scan), three-dimensional scanner 2 reacquires pieces of three-dimensional data including the positions of a plurality of points representing the surface of a scan object.

When pieces of three-dimensional data are sequentially inputted from three-dimensional scanner 2, data processing apparatus 1 generates virtual space 50 with reference to positions (detected positions) included in the inputted three-dimensional data.

For example, when a position B of a point is detected in the N+1-th scan as illustrated in FIG. 7(C), data processing apparatus 1 generates cylindrical virtual space 50 with the central axis located on optical axis L passing through detected position B as illustrated in FIG. 7(D). When virtual space 50 is generated for three-dimensional data (three-dimensional data including position information on detected position B) acquired in the N+1-th scan, data processing apparatus 1 determines whether three-dimensional data acquired before the N+1-th scan (for example, in the N-th scan in the past) is present in virtual space 50.

Data processing apparatus 1 determines whether three-dimensional data acquired in the past is present in the direction of optical axis L to the scanner position from a point corresponding to detected position B serving as a reference position for generating virtual space 50.

When determining whether three-dimensional data acquired before the N+1-th scan (in the N-th scan) is present in virtual space 50, data processing apparatus 1 aligns the origin point (fiducial point) of the coordinates of the three-dimensional data in the N+1-th scan with the origin point (fiducial point) of the coordinates of the three-dimensional data in the N-th scan. For example, data processing apparatus 1 transforms the coordinates of the three-dimensional data in the N+1-th scan according to the coordinate system of three-dimensional data in the N-th scan. Thus, data processing apparatus 1 can compare the three-dimensional data in the N-th scan and the three-dimensional data in the N+1-th scan.

Data processing apparatus 1 may use a scanner position at the time of the acquisition of the three-dimensional data in the N-th scan as the origin point (fiducial point). Specifically, data processing apparatus 1 may cause the coordinates of a scanner position at the time of the acquisition of the three-dimensional data in the N+1-th scan to match with the coordinates of the scanner position at the time of the acquisition of the three-dimensional data in the N-th scan and compare the three-dimensional data in the N-th scan and the three-dimensional data in the N+1-th scan in the coordinate system with the scanner position as the origin point.

In the example of FIG. 7(D), three-dimensional data acquired in the N-th scan is present in virtual space 50 for the three-dimensional data acquired in the N+1-th scan. Thus, data processing apparatus 1 verifies whether the three-dimensional data in the N-th scan and the three-dimensional data in the N+1-th scan are true or not by comparing the three-dimensional data in the N-th scan and the three-dimensional data in the N+1-th scan.

Specifically, data processing apparatus 1 according to the present embodiment determines that the three-dimensional data inputted later in the N+1-th scan is true three-dimensional data in the comparison between the three-dimensional data in the N-th scan and the three-dimensional data in the N+1-th scan.

For example, as illustrated in FIGS. 9(A) to 9(C), it is assumed that data processing apparatus 1 receives a plurality of three-dimensional data pieces a to c in a specific area in an oral cavity in the N-th scan of three-dimensional scanner 2, and then as illustrated in FIGS. 9(D) to 9(F), data processing apparatus 1 receives a plurality of three-dimensional data pieces d to f again in the same specific area in the oral cavity in the N+1-th scan of three-dimensional scanner 2.

Upon receipt of three-dimensional data piece d in the N+1-th scan as illustrated in FIG. 9(D), data processing apparatus 1 generates virtual space 50 for three-dimensional data piece d and determines whether three-dimensional data inputted before the N+1-th scan (for example, in the N-th scan in the past) is present in virtual space 50. If three-dimensional data piece a inputted in the past N-th scan is present in virtual space 50 for three-dimensional data piece d inputted in the N+1-th scan, data processing apparatus 1 compares the timings of input between three-dimensional data piece a in the N-th scan and three-dimensional data piece d in the N+1-th scan and determines that three-dimensional data piece d inputted later in the N+1-th scan is true three-dimensional data. In other words, data processing apparatus 1 determines that the three-dimensional data piece d inputted this time is true three-dimensional data.

Upon receipt of three-dimensional data piece e in the N+1-th scan as illustrated in FIG. 9(E), data processing apparatus 1 generates virtual space 50 for three-dimensional data piece e and determines whether three-dimensional data inputted before the N+1-th scan (for example, in the N-th scan in the past) is present in virtual space 50. If three-dimensional data piece b inputted in the past N-th scan is present in virtual space 50 for three-dimensional data piece e inputted in the N+1-th scan, data processing apparatus 1 compares the timings of input between three-dimensional data piece b in the N-th scan and three-dimensional data piece e in the N+1-th scan and determines that three-dimensional data piece e inputted later in the N+1-th scan is true three-dimensional data. In other words, data processing apparatus 1 determines that three-dimensional data piece e inputted this time is true three-dimensional data.

Upon receipt of three-dimensional data piece f in the N+1-th scan as illustrated in FIG. 9(F), data processing apparatus 1 generates virtual space 50 for three-dimensional data piece f and determines whether three-dimensional data inputted before the N+1-th scan (for example, in the N-th scan in the past) is present in virtual space 50. If three-dimensional data piece c inputted in the past N-th scan is present in virtual space 50 for three-dimensional data piece f inputted in the N+1-th scan, data processing apparatus 1 compares the timings of input between three-dimensional data piece c in the N-th scan and three-dimensional data piece f in the N+1-th scan and determines that three-dimensional data piece f inputted later in the N+1-th scan is true three-dimensional data. In other words, data processing apparatus 1 determines that the three-dimensional data piece f inputted this time is true three-dimensional data. Specifically, if pieces of three-dimensional data are present in the virtual space, data processing apparatus 1 determines that three-dimensional data piece f, which is the latest scanned and inputted three-dimensional data, is true data.

In this way, arithmetic unit 11 (data processing unit 1102) of data processing apparatus 1 compares the timings of input between the N-th three-dimensional data inputted from input unit 1101 and the N+1-th three-dimensional data inputted from input unit 1101 in virtual space 50 set with respect to the scanner position and determines that the N+1-th three-dimensional data inputted later from input unit 1101 is true three-dimensional data. In the foregoing example, if the N-th three-dimensional data is applied to "first three-dimensional data," the N+1-th three-dimensional data is applied to "second three-dimensional data," and if the N-th three-dimensional data is applied to "second three-dimensional data," the N+1-th three-dimensional data is applied to "first three-dimensional data."

By performing the data verification, as illustrated in FIG. 9(G), data processing apparatus 1 sets only three-dimensional data pieces d to f, which are inputted later from input unit 1101, as true three-dimensional data and then generates, only on the basis of true three-dimensional data pieces d to f, two-dimensional image data corresponding to a two-dimensional image viewed from any viewpoint. In one embodiment, data processing apparatus 1 stores true three-dimensional data pieces d to f.

Hence, for example, as illustrated in FIG. 5(A), even if obstacles such as a finger enter scan range R of three-dimensional scanner 2 during the N-th scan, the user removes the obstacles and then scans a scan object again at the same point in the N+1-th scan, so that data processing apparatus 1 can set only the three-dimensional data inputted later in the N+1-th scan as true three-dimensional data. Thus, the user does not need to select true three-dimensional data from three-dimensional data acquired by three-dimensional scanner 2, thereby simply and properly acquiring three-dimensional data on a scan object through three-dimensional scanner 2. In other words, when an obstacle is displayed with a scanned object on display 3, the object is rescanned at the same position after the obstacle is removed, so that the object is displayed without the obstacle. This allows the user to confirm the storage of true three-dimensional data written over false three-dimensional data.

If data processing apparatus 1 determines that three-dimensional data inputted later is true three-dimensional data among a plurality of three-dimensional data pieces, for example, if a finger does not enter an oral cavity in the N-th scan but enters the oral cavity in the N+1-th scan, three-dimensional data on the surface of the finger may be erroneously set as true three-dimensional data. However, the user usually scans an oral cavity while viewing a two-dimensional image (a two-dimensional image that is generated on the basis of three-dimensional data and is viewed from any viewpoint) displayed on display 3. Thus, when the generation of a two-dimensional image of a finger viewed from any viewpoint is recognized, teeth are rescanned at the same point after the finger is removed, so that data processing apparatus 1 can set only subsequently inputted three-dimensional data as true three-dimensional data.

[Three-Dimensional Data Table]

Referring to FIG. 10, a three-dimensional data table will be described below. FIG. 10 shows an example of the three-dimensional data table. When three-dimensional data inputted from input unit 1101 is stored as three-dimensional data 121, data processing apparatus 1 stores the three-dimensional data in a table format shown in FIG. 10.

As illustrated in FIG. 10, in the three-dimensional data table, a data type is assigned to each of the three-dimensional data pieces of points representing the surface of a scan object after the three-dimensional data pieces are inputted from input unit 1101. Furthermore, the three-dimensional data table stores position information and color information that are included in the three-dimensional data pieces of the points representing the surface of the scan object after the three-dimensional data pieces are inputted from input unit 1101. The position information includes the positions of the points (the coordinates in axes in vertical, horizontal, and height directions). The color information includes the colors of the points (e.g., RGB values).

Moreover, in the three-dimensional data table, a deletion flag is assigned to each of the three-dimensional data pieces of the points representing the surface of the scan object after the three-dimensional data pieces are inputted from input unit 1101. The deletion flag includes information for specifying whether three-dimensional data is used when two-dimensional image data (data corresponding to a two-dimensional image that is generated on the basis of three-dimensional data and is viewed from any viewpoint) is generated. For example, data processing apparatus 1 does not set the deletion flag (stores a "0" bit) for three-dimensional data used when the two-dimensional image data is generated, and sets the deletion flag (stores a "1" bit) for three-dimensional data unused when the two-dimensional image data is generated. In other words, data processing apparatus 1 does not set the deletion flag for three-dimensional data verified as true data in data verification and sets the deletion flag as an index of falsehood for three-dimensional data verified as false data in data verification.

[Mesh Generation, Data Set Verification, and Image Data Generation]

Figure 11:
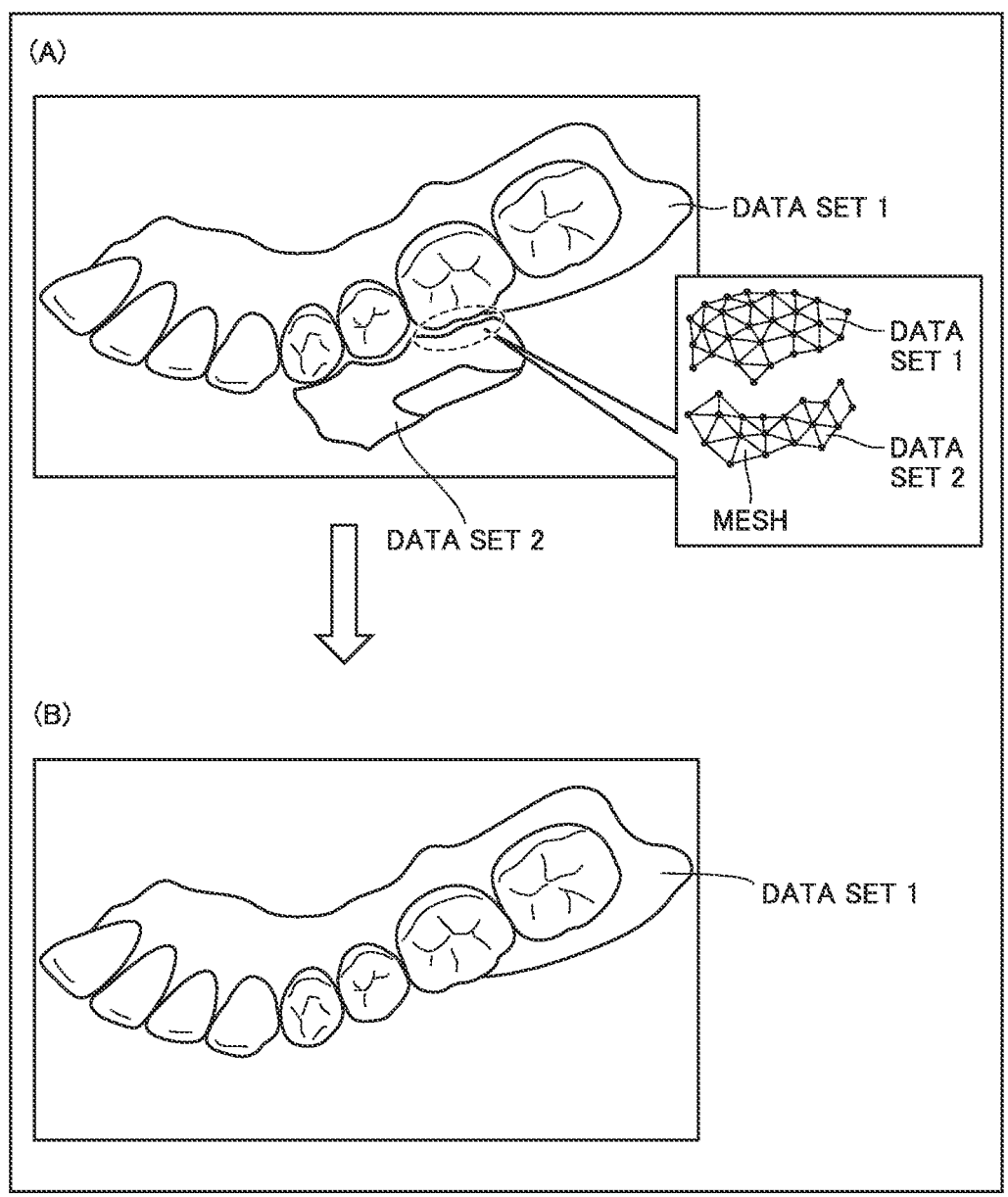
FIG. 11 illustrates an example of mesh generation, data set verification, and image data generation by the data processing apparatus according to the present embodiment.

Referring to FIG. 11, mesh generation, data set verification, and image data generation by data processing apparatus 1 according to the present embodiment will be described below. FIG. 11 illustrates an example of mesh generation, data set verification, and image data generation by data processing apparatus 1 according to the present embodiment.

Data processing unit 1102 of data processing apparatus 1 generates a data set by performing mesh generation, verifies a data set by performing data set verification, and generates two-dimensional image data, which is generated on the basis of three-dimensional data and corresponds to a two-dimensional image viewed from any viewpoint, by performing image data generation.

Specifically, data processing apparatus 1 generates at least one data set by connecting a plurality of three-dimensional data pieces present in a predetermined range among three-dimensional data pieces acquired by three-dimensional scanner 2.

For example, as illustrated in FIG. 11(A), data processing apparatus 1 generates one mesh by connecting at least three three-dimensional data pieces via straight lines in the predetermined range. In this example, data processing apparatus 1 generates a triangular mesh by connecting three-dimensional data pieces via straight lines. Four three-dimensional data pieces may be connected via straight lines to generate a quadrangular mesh, or five or more three-dimensional data pieces may be connected via straight lines to generate a mesh.

Data processing apparatus 1 generates a plurality of meshes in the above-mentioned manner and connects the meshes to generate a data set. Specifically, a plurality of three-dimensional data pieces included in a data set are each connected to at least one of other three-dimensional data pieces present in the predetermined range, so that a mesh is formed. The larger the number of connected three-dimensional data pieces, the larger the amount of three-dimensional data (e.g., the number of three-dimensional data pieces) included in a data set.

Moreover, data processing apparatus 1 verifies a plurality of three-dimensional data pieces by performing data verification on the three-dimensional data pieces included in a generated data set.

Data processing apparatus 1 then sets a data set with the largest data amount as a true data set among a plurality of data sets through data set verification.

For example, as illustrated in FIG. 11(A), data processing apparatus 1 generates a data set 1 by using a plurality of three-dimensional data pieces representing the surfaces of tooth parts and generates a data set 2 by using a plurality of three-dimensional data pieces representing the surfaces of obstacles such as a finger. In this case, as illustrated in FIG. 11(B), data set 1 with the largest data amount is set as a true data set from data sets 1 and 2.

Subsequently, through image data generation, data processing apparatus 1 generates two-dimensional image data, which corresponds to a two-dimensional image viewed from any viewpoint, on the basis of the true data set with the largest data amount.

As described above, a data set includes a plurality of three-dimensional data pieces present in a predetermined range and thus three-dimensional data pieces outside the predetermined range are not included in the data set. Since the surfaces of teeth are continuous in an oral cavity, the data set with the largest data amount is highly likely to include a plurality of three-dimensional data pieces representing the surfaces of teeth. During a scan, an operator may pull a patient's lip outward with a finger. In this case, the operator's finger may be scanned by three-dimensional scanner 2. Since the operator's finger is placed outside the oral cavity, three-dimensional data on points constituting the finger is unlikely to be present in a predetermined range of three-dimensional data on points constituting teeth. Thus, data processing apparatus 1 can discriminate three-dimensional data on points constituting teeth from three-dimensional data on points constituting a finger.

As described above, if data set 1 and data set 2 are generated by using a plurality of three-dimensional data pieces acquired by three-dimensional scanner 2, data processing apparatus 1 generates two-dimensional data, which corresponds to a two-dimensional image viewed from any viewpoint, on the basis of data set 1 with the largest data amount in data sets 1 and 2, so that data set 1 generated on the basis of a plurality of three-dimensional data pieces representing the surfaces of tooth portions can be an object to be outputted. In other words, data processing apparatus 1 can exclude data set 2, which is generated on the basis of a plurality of three-dimensional data pieces representing the surface of an obstacle, from objects to be outputted. Thus, the user does not need to select a plurality of three-dimensional data pieces representing the surfaces of tooth portions from three-dimensional data acquired by three-dimensional scanner 2, thereby simply and properly acquiring three-dimensional data on a scan object through three-dimensional scanner 2.

[Data Set Table]

Referring to FIG. 12, a data set table will be described below. FIG. 12 shows an example of the data set table. Data processing apparatus 1 stores a data set generated on the basis of three-dimensional data inputted from input unit 1101, in a table format shown in FIG. 12.

As illustrated in FIG. 12, in the data set table, a data set type is assigned to each of generated data sets. The data set table stores the number of meshes constituting each of the data sets.

Data processing apparatus 1 generates a data set by performing mesh generation and then stores the number of meshes assigned with a data set type in the data set table. Data processing apparatus 1 stores the number of meshes for each of generated data sets in the data set table, thereby classifying a plurality of inputted three-dimensional data pieces into data sets.

Furthermore, data processing apparatus 1 can select a data set (data set 1 in this example) with the largest amount of data (the largest number of meshes) with reference to the data set table and generate two-dimensional image data, which corresponds to a two-dimensional image viewed from any viewpoint, on the basis of the selected data set.

[Processing Flow of Data Processing Apparatus 1]

Figure 13:
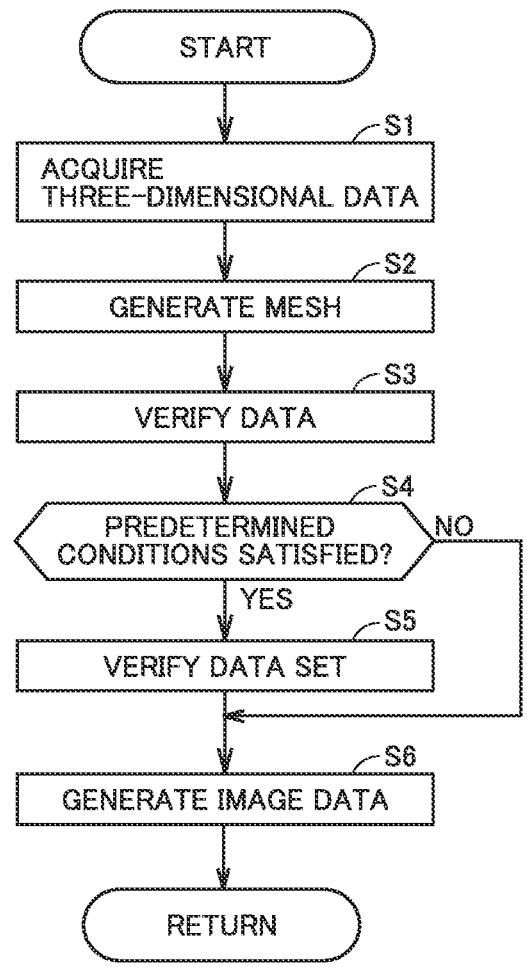
FIG. 13 is a flowchart for explaining an example of processing performed by the data processing apparatus according to the present embodiment.

Referring to FIG. 13, a processing flow performed by data processing apparatus 1 according to the present embodiment will be described below. FIG. 13 is a flowchart for explaining an example of processing performed by data processing apparatus 1 according to the present embodiment. Steps (hereinafter denoted as "S") in FIG. 13 are implemented by executing data processing program 122 by arithmetic unit 11 of data processing apparatus 1. After the start of a scan by three-dimensional scanner 2, data processing apparatus 1 repeatedly performs the processing of the flowchart in FIG. 13 at predetermined intervals (e.g., several milliseconds). When data processing apparatus 1 or three-dimensional scanner 2 is turned off or when a scan by three-dimensional scanner 2 is stopped, data processing apparatus 1 terminates the processing of the flowchart in FIG. 13.

As indicated in FIG. 13, data processing apparatus 1 acquires three-dimensional data on a point scanned by three-dimensional scanner 2 (S1).

Data processing apparatus 1 generates a data set by generating at least one mesh by using the three-dimensional data acquired by three-dimensional scanner 2 (S2). Data processing apparatus 1 performs data verification to verify the three-dimensional data acquired by three-dimensional scanner 2 (S3).

In the data verification of S3, as described with reference to FIGS. 7 to 9, data processing apparatus 1 generates virtual space 50 on the basis of positions where points included in the three-dimensional data inputted in S1 are detected (detected positions) and the scanner position. Data processing apparatus 1 then determines whether virtual space 50 includes three-dimensional data acquired by a scan preceding the acquisition of the three-dimensional data to be verified. If virtual space 50 includes three-dimensional data acquired by a scan preceding the acquisition of the three-dimensional data to be verified, data processing apparatus 1 determines that the three-dimensional data to be verified is true three-dimensional data. For other three-dimensional data pieces that are not verified as true three-dimensional data, data processing apparatus 1 sets the deletion flag in the three-dimensional data table.

Subsequently, data processing apparatus 1 determines whether predetermined conditions are satisfied (S4). The predetermined conditions include a condition that the data amount of three-dimensional data inputted from input unit 1101 exceeds a first predetermined amount (e.g., 100 data pieces). The predetermined conditions may include a condition that a time for inputting three-dimensional data from input unit 1101 exceeds a predetermined time. For example, the predetermined condition may be satisfied when an elapsed time from the start of the processing of the flowchart in FIG. 13 exceeds the predetermined time. In one embodiment, the predetermined condition may be satisfied when an elapsed time from the determination of YES at S4 in the previous processing exceeds the predetermined time in the repeated processing of the flowchart in FIG. 13.

Furthermore, the predetermined conditions may be satisfied when an elapsed time from the start of the processing of the flowchart in FIG. 13 exceeds the predetermined time and the data amount of three-dimensional data inputted from input unit 1101 exceeds a second predetermined amount (e.g., the average of a data amount acquired according to an acquisition time). In one embodiment, the predetermined conditions may be satisfied when an elapsed time from the determination of YES at S4 in the previous processing exceeds the predetermined time and the data amount of three-dimensional data inputted from input unit 1101 exceeds the second predetermined amount (e.g., the average of a data amount acquired according to an acquisition time). This is because if the second predetermined amount is set at the average of a data amount acquired according to an acquisition time, three-dimensional data representing the surfaces of obstacles such as a finger may be acquired when the data amount of three-dimensional data inputted from input unit 1101 exceeds the second predetermined amount.

As described above, the predetermined conditions include at least one of the condition that the data amount of three-dimensional data inputted from input unit 1101 exceeds the predetermined amount and the condition that a time for inputting three-dimensional data from input unit 1101 exceeds the predetermined time.

If the predetermined conditions are satisfied (YES at S4), data processing apparatus 1 sets a data set with the largest data amount as a true data set among a plurality of data sets by performing data set verification (S5).

If the predetermined conditions are not satisfied (NO at S4) or after S5, data processing apparatus 1 generates two-dimensional image data, which corresponds to a two-dimensional image viewed from any viewpoint, on the basis of the true data set by performing image data generation (S6). The two-dimensional image data generated in S6 is outputted to an external device, e.g., display 3 through output unit 1104.

As described above, by performing the data verification, data processing apparatus 1 according to the present embodiment compares three-dimensional data acquired in S1 this time and three-dimensional data acquired in S1 in the past in virtual space 50 set with respect to the scanner position and verifies the three-dimensional data acquired in S1 this time and the three-dimensional data acquired in S1 in the past. Thus, the user does not need to select true three-dimensional data from three-dimensional data acquired by three-dimensional scanner 2, thereby simply and properly acquiring three-dimensional data on a scan object through three-dimensional scanner 2.

Moreover, by performing mesh generation, data processing apparatus 1 according to the present embodiment generates data sets by using a plurality of three-dimensional data pieces located in a predetermined range from among three-dimensional data pieces acquired in S1 this time and in the past. By performing data set verification, data processing apparatus 1 sets a data set with the largest data amount as a true data set among a plurality of data sets. Furthermore, data processing apparatus 1 generates image data on the basis of the true data set. Thus, the user does not need to select a plurality of three-dimensional data pieces representing the surfaces of tooth portions from three-dimensional data acquired by three-dimensional scanner 2, thereby simply and properly acquiring three-dimensional data on a scan object through three-dimensional scanner 2.

A user, e.g., a dentist acquires three-dimensional data on an object (e.g., a dental arch) in an oral cavity by using three-dimensional scanner 2 and stores the acquired three-dimensional data in data processing apparatus 1. The user then outputs the three-dimensional data stored in data processing apparatus 1 to a milling machine or a 3D machine and displays a two-dimensional image viewed from any viewpoint on display 3 on the basis of the three-dimensional data in order to make a portion being treated and a state of a patient's tooth row understandable by a patient.

To allow the user to understand the current degree of accuracy of acquired and recorded three-dimensional data on a dental arch, data processing apparatus 1 displays a two-dimensional image of a dental arch viewed from any viewpoint on display 3 in real time on the basis of correctly acquired and recorded three-dimensional data.

In the process of acquiring and recording three-dimensional data on an object, e.g., a dental arch in an oral cavity, data processing apparatus 1 generates data sets by using three-dimensional data through mesh generation, verifies three-dimensional data included in the data sets through data verification, sets the deletion flag for false three-dimensional data, verifies the data sets through data set verification, and generates two-dimensional image data on the basis of the true data set. In a process from the acquisition of three-dimensional data to the generation of two-dimensional image data, data processing apparatus 1 only sets the deletion flag for false three-dimensional data and does not delete the false three-dimensional data or regenerate a data set only based on true three-dimensional data. Two-dimensional image data is generated only on the basis of true three-dimensional data and a true data set without using false three-dimensional data with the set deletion flag. In other words, data processing apparatus 1 leaves recorded false three-dimensional data but does not display the false three-dimensional data on display 3. After the timing of the completion of the acquisition and recording of a series of three-dimensional data by the user through three-dimensional scanner 2 (for example, the timing of the turnoff of data processing apparatus 1 or three-dimensional scanner 2 or the timing of the stop of a scan through three-dimensional scanner 2), data processing apparatus 1 deletes the false three-dimensional data with the set deletion flag from records. Thus, data processing apparatus 1 can avoid a processing load caused by deleting false three-dimensional data or regenerating a data set only based on true three-dimensional data in the processing flow of FIG. 13.

[Modification]

The present disclosure is not limited to the foregoing example and can be modified and applied in various ways. A modification applicable to the present disclosure will be described below. Regarding data processing apparatus 1 according to the modification, only different configurations and functions from data processing apparatus 1 according to the present embodiment will be described below. Other configurations and functions of data processing apparatus 1 according to the modification are assumed to be identical to those of data processing apparatus 1 according to the present embodiment.

(Data Verification)

Figure 14:
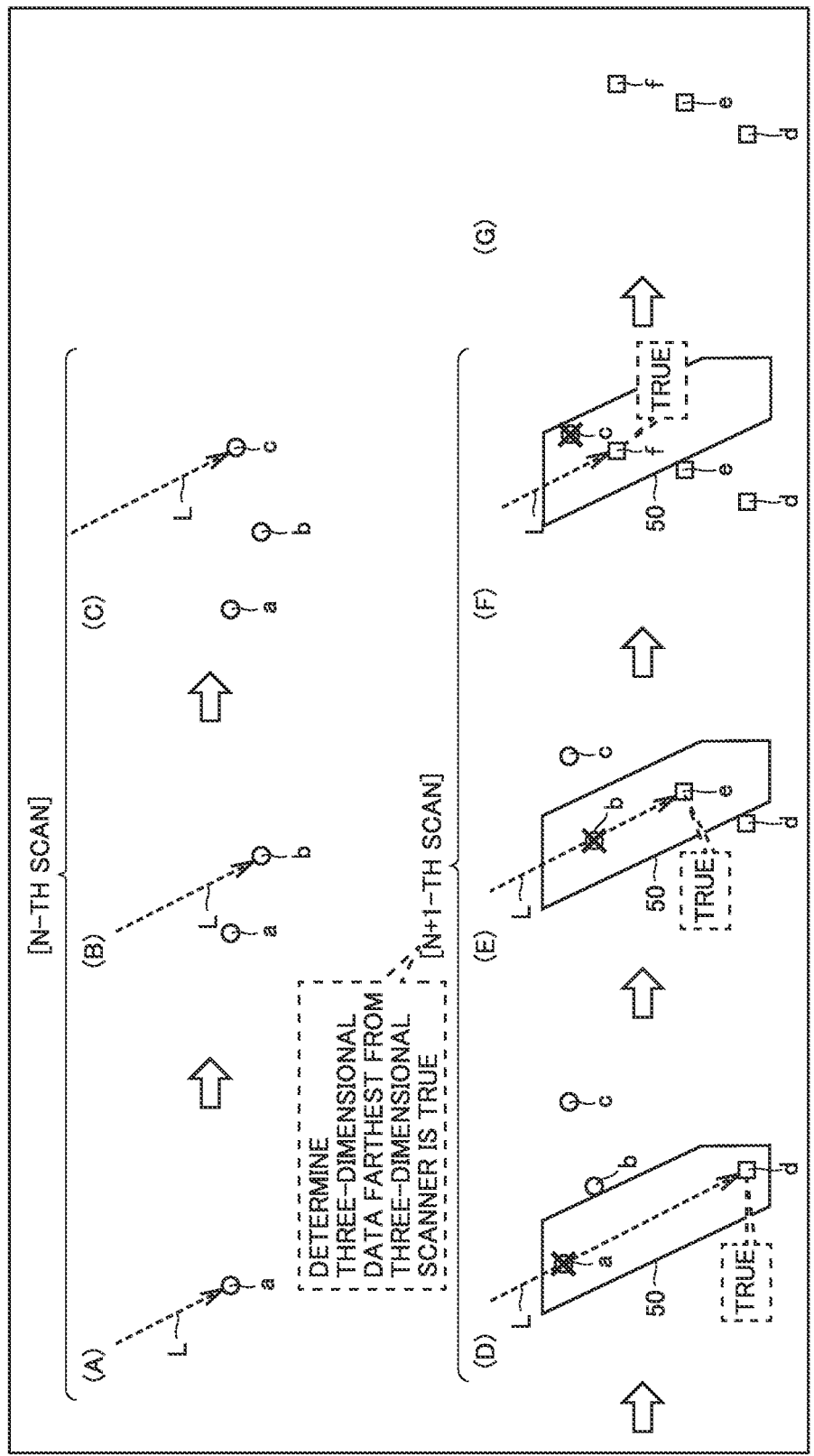
FIG. 14 illustrates an example of the data verification of the data processing apparatus according to a modification.
Figure 15:
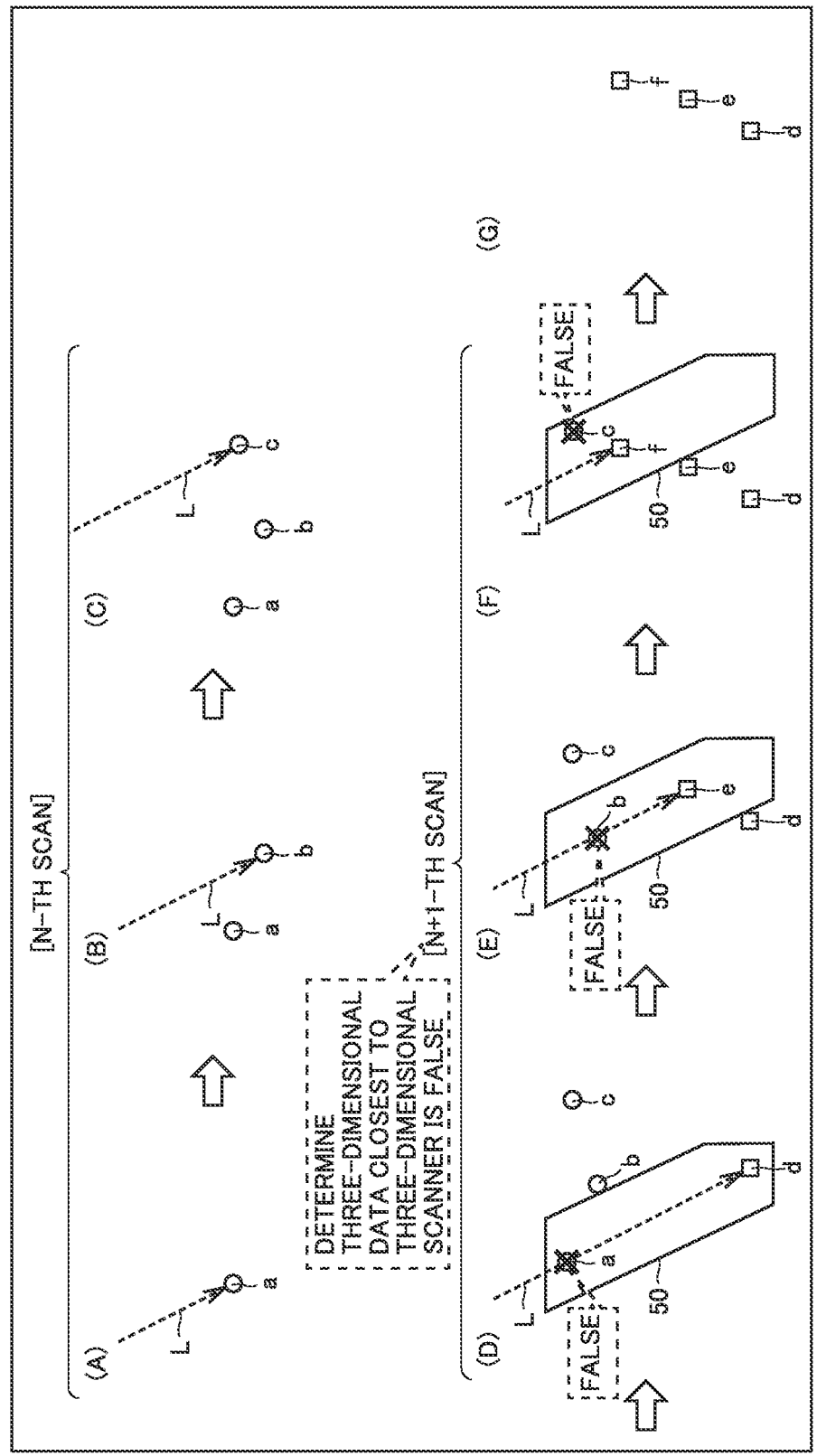
FIG. 15 illustrates an example of the data verification of the data processing apparatus according to the modification.
Figure 16:
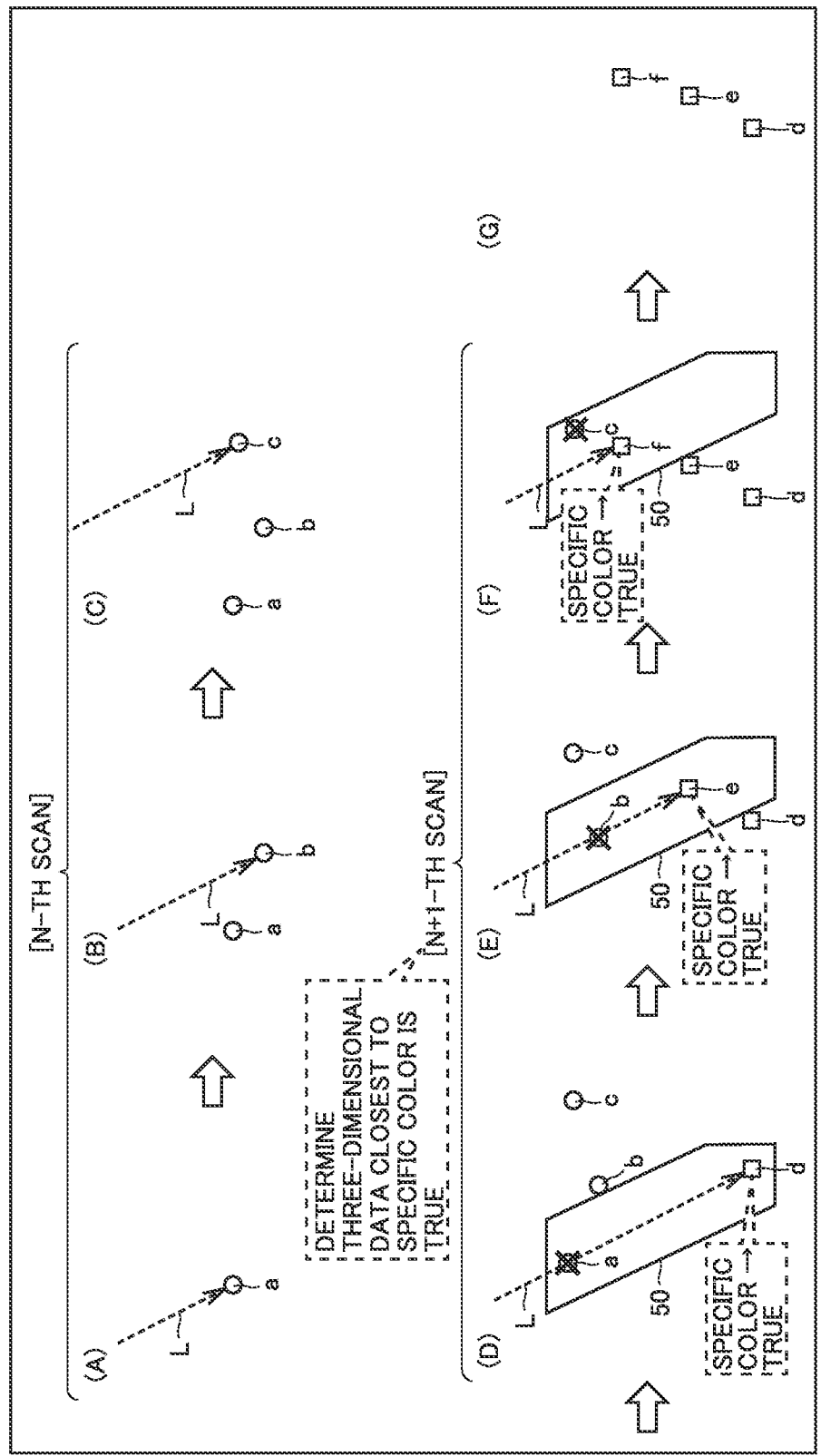
FIG. 16 illustrates an example of the data verification of the data processing apparatus according to the modification.

Data processing apparatus 1 according to the present embodiment determines that three-dimensional data inputted later is true three-dimensional data among a plurality of inputted three-dimensional data pieces through data verification. As illustrated in FIGS. 14 to 16, data processing apparatus 1 according to the modification may verify three-dimensional data from a different aspect from the data verification according to the present embodiment. FIGS. 14 to 16 illustrate an example of the data verification of data processing apparatus 1 according to the modification.

Through data verification, data processing apparatus 1 according to the modification may determine that three-dimensional data including the position of the farthest point from the scanner position is true three-dimensional data among a plurality of inputted three-dimensional data pieces.

For example, as illustrated in FIGS. 14(A) to 14(C), it is assumed that data processing apparatus 1 receives a plurality of three-dimensional data pieces a to c in a specific area in an oral cavity in the N-th scan of three-dimensional scanner 2, and then as illustrated in FIGS. 14(D) to 14(F), data processing apparatus 1 receives a plurality of three-dimensional data pieces d to f again in the same specific area in the oral cavity in the N+1-th scan of three-dimensional scanner 2.

Upon receipt of three-dimensional data piece d in the N+1-th scan as illustrated in FIG. 14(D), data processing apparatus 1 generates virtual space 50 for three-dimensional data piece d and determines whether three-dimensional data inputted before the N+1-th scan (for example, in the N-th scan in the past) is present in virtual space 50. If three-dimensional data piece a inputted in the past N-th scan is present in virtual space 50 for three-dimensional data piece d inputted in the N+1-th scan, data processing apparatus 1 compares distances from a scanner position between three-dimensional data piece a in the N-th scan and three-dimensional data piece d in the N+1-th scan and determines that three-dimensional data piece d including the position of the farthest point from the scanner position in the N+1-th scan is true three-dimensional data.

Upon receipt of three-dimensional data piece e in the N+1-th scan as illustrated in FIG. 14(E), data processing apparatus 1 generates virtual space 50 for three-dimensional data piece e and determines whether three-dimensional data inputted before the N+1-th scan (for example, in the N-th scan in the past) is present in virtual space 50. If three-dimensional data piece b inputted in the past N-th scan is present in virtual space 50 for three-dimensional data piece e inputted in the N+1-th scan, data processing apparatus 1 compares distances from the scanner position between three-dimensional data piece b in the N-th scan and three-dimensional data piece e in the N+1-th scan and determines that three-dimensional data piece e including the position of the farthest point from the scanner position in the N+1-th scan is true three-dimensional data.

Upon receipt of three-dimensional data piece fin the N+1-th scan as illustrated in FIG. 14(F), data processing apparatus 1 generates virtual space 50 for three-dimensional data piece f and determines whether three-dimensional data inputted before the N+1-th scan (for example, in the N-th scan in the past) is present in virtual space 50. If three-dimensional data piece c inputted in the past N-th scan is present in virtual space 50 for three-dimensional data piece f inputted in the N+1-th scan, data processing apparatus 1 compares distances from the scanner position between three-dimensional data piece c in the N-th scan and three-dimensional data piece fin the N+1-th scan and determines that three-dimensional data piece f including the position of the farthest point from the scanner position in the N+1-th scan is true three-dimensional data.

In this way, arithmetic unit 11 (data processing unit 1102) of data processing apparatus 1 according to the modification compares distances from the scanner position between the N-th three-dimensional data inputted from input unit 1101 and the N+1-th three-dimensional data inputted from input unit 1101 in virtual space 50 set with respect to the scanner position and determines that the three-dimensional data including the position of the farthest point from the scanner position is true three-dimensional data. In the foregoing example, if the N-th three-dimensional data is applied to "first three-dimensional data," the N+1-th three-dimensional data is applied to "second three-dimensional data," and if the N-th three-dimensional data is applied to "second three-dimensional data," the N+1-th three-dimensional data is applied to "first three-dimensional data."

If data processing apparatus 1 determines that three-dimensional data including the position of the farthest point from the scanner position is true three-dimensional data among a plurality of three-dimensional data pieces, for example, when the user first scans one side of a specific tooth near the user and then scans the other side of the same specific tooth away from the user, data processing apparatus 1 may determine that only the three-dimensional data on the other side of the specific tooth away from the user is true three-dimensional data. However, as illustrated in FIG. 7, data processing apparatus 1 determines whether three-dimensional data acquired in the past is present in the direction of optical axis L to the scanner position from a point corresponding to the detected position serving as a reference position for generating virtual space 50, so that the foregoing problem does not occur.

Through data verification, data processing apparatus 1 according to the modification may determine that three-dimensional data including the position of the closest point to the scanner position is false three-dimensional data among a plurality of inputted three-dimensional data pieces.

For example, as illustrated in FIGS. 15(A) to 15(C), it is assumed that data processing apparatus 1 receives a plurality of three-dimensional data pieces a to c in a specific area in an oral cavity in the N-th scan of three-dimensional scanner 2, and then as illustrated in FIGS. 15(D) to 15(F), data processing apparatus 1 receives a plurality of three-dimensional data pieces d to f again in the same specific area in the oral cavity in the N+1-th scan of three-dimensional scanner 2.

Upon receipt of three-dimensional data piece d in the N+1-th scan as illustrated in FIG. 15(D), data processing apparatus 1 generates virtual space 50 for three-dimensional data piece d and determines whether three-dimensional data inputted before the N+1-th scan (for example, in the N-th scan in the past) is present in virtual space 50. If three-dimensional data piece a inputted in the past N-th scan is present in virtual space 50 for three-dimensional data piece d inputted in the N+1-th scan, data processing apparatus 1 compares distances from the scanner position between three-dimensional data piece a in the N-th scan and three-dimensional data piece d in the N+1-th scan and determines that three-dimensional data piece a including the position of the closest point to the scanner position in the N-th scan is false three-dimensional data. In other words, data processing apparatus 1 determines that the three-dimensional data piece d in the N+1-th scan is true three-dimensional data.

Upon receipt of three-dimensional data piece e in the N+1-th scan as illustrated in FIG. 14(E), data processing apparatus 1 generates virtual space 50 for three-dimensional data piece e and determines whether three-dimensional data inputted before the N+1-th scan (for example, in the N-th scan in the past) is present in virtual space 50. If three-dimensional data piece b inputted in the past N-th scan is present in virtual space 50 for three-dimensional data piece e inputted in the N+1-th scan, data processing apparatus 1 compares distances from the scanner position between three-dimensional data piece b in the N-th scan and three-dimensional data piece e in the N+1-th scan and determines that three-dimensional data piece b including the position of the closest point to the scanner position in the N-th scan is false three-dimensional data. In other words, data processing apparatus 1 determines that three-dimensional data piece e in the N+1-th scan is true three-dimensional data.

Upon receipt of three-dimensional data piece f in the N+1-th scan as illustrated in FIG. 14(F), data processing apparatus 1 generates virtual space 50 for three-dimensional data piece f and determines whether three-dimensional data inputted before the N+1-th scan (for example, in the N-th scan in the past) is present in virtual space 50. If three-dimensional data piece c inputted in the past N-th scan is present in virtual space 50 for three-dimensional data piece f inputted in the N+1-th scan, data processing apparatus 1 compares distances from the scanner position between three-dimensional data piece c in the N-th scan and three-dimensional data piece f in the N+1-th scan and determines that three-dimensional data piece c including the position of the closest point to the scanner position in the N-th scan is false three-dimensional data. In other words, data processing apparatus 1 determines that three-dimensional data piece f in the N+1-th scan is true three-dimensional data.

In this way, arithmetic unit 11 (data processing unit 1102) of data processing apparatus 1 according to the modification compares distances from the scanner position between the N-th three-dimensional data inputted from input unit 1101 and the N+1-th three-dimensional data inputted from input unit 1101 in virtual space 50 set with respect to the scanner position and determines that the three-dimensional data including the position of the closest point to the scanner position is false three-dimensional data. In the foregoing example, if the N-th three-dimensional data is applied to "first three-dimensional data," the N+1-th three-dimensional data is applied to "second three-dimensional data," and if the N-th three-dimensional data is applied to "second three-dimensional data," the N+1-th three-dimensional data is applied to "first three-dimensional data."

If data processing apparatus 1 determines that three-dimensional data including the position of the closest point to the scanner position is false three-dimensional data among a plurality of three-dimensional data pieces, for example, when the user first scans one side of a specific tooth near the user and then scans the other side of the same specific tooth away from the user, data processing apparatus 1 may determine that the three-dimensional data on the other side of the specific tooth near the user is false three-dimensional data. However, as illustrated in FIG. 7, data processing apparatus 1 determines whether three-dimensional data acquired in the past is present in the direction of optical axis L to the scanner position from a point corresponding to the detected position serving as a reference position for generating virtual space 50, so that the foregoing problem does not occur.

Through data verification, data processing apparatus 1 according to the modification may determine that three-dimensional data including color information on the closest color to a specific color is true three-dimensional data among a plurality of inputted three-dimensional data pieces. The specific color may be white close to a tooth color and can be properly set by the user. Data processing apparatus 1 can specify the colors of points corresponding to three-dimensional data by referring to the color information on three-dimensional data stored in the three-dimensional data table in FIG. 10.

For example, as illustrated in FIGS. 16(A) to 16(C), it is assumed that data processing apparatus 1 receives a plurality of three-dimensional data pieces a to c in a specific area in an oral cavity in the N-th scan of three-dimensional scanner 2, and then as illustrated in FIGS. 16(D) to 16(F), data processing apparatus 1 receives a plurality of three-dimensional data pieces d to f again in the same specific area in the oral cavity in the N+1-th scan of three-dimensional scanner 2.

Upon receipt of three-dimensional data piece d in the N+1-th scan as illustrated in FIG. 16(D), data processing apparatus 1 generates virtual space 50 for three-dimensional data piece d and determines whether three-dimensional data inputted before the N+1-th scan (for example, in the N-th scan in the past) is present in virtual space 50. If three-dimensional data piece a inputted in the past N-th scan is present in virtual space 50 for three-dimensional data piece d inputted in the N+1-th scan, data processing apparatus 1 compares color information included in three-dimensional data piece a in the N-th scan and color information included in three-dimensional data piece d in the N+1-th scan and determines that three-dimensional data piece d including color information on the closest color to the specific color in the N+1-th scan is true three-dimensional data.

Upon receipt of three-dimensional data piece e in the N+1-th scan as illustrated in FIG. 16(E), data processing apparatus 1 generates virtual space 50 for three-dimensional data piece e and determines whether three-dimensional data inputted before the N+1-th scan (for example, in the N-th scan in the past) is present in virtual space 50. If three-dimensional data piece b inputted in the past N-th scan is present in virtual space 50 for three-dimensional data piece e inputted in the N+1-th scan, data processing apparatus 1 compares color information included in three-dimensional data piece b in the N-th scan and color information included in three-dimensional data piece e in the N+1-th scan and determines that three-dimensional data piece e including color information on the closest color to the specific color in the N+1-th scan is true three-dimensional data.

Upon receipt of three-dimensional data piece f in the N+1-th scan as illustrated in FIG. 16(F), data processing apparatus 1 generates virtual space 50 for three-dimensional data piece f and determines whether three-dimensional data inputted before the N+1-th scan (for example, in the N-th scan in the past) is present in virtual space 50. If three-dimensional data piece c inputted in the past N-th scan is present in virtual space 50 for three-dimensional data piece f inputted in the N+1-th scan, data processing apparatus 1 compares color information included in three-dimensional data piece c in the N-th scan and color information included in three-dimensional data piece fin the N+1-th scan and determines that three-dimensional data piece f including color information on the closest color to the specific color in the N+1-th scan is true three-dimensional data.

In this way, arithmetic unit 11 (data processing unit 1102) of data processing apparatus 1 according to the modification compares color information between the N-th three-dimensional data inputted from input unit 1101 and the N+1-th three-dimensional data inputted from input unit 1101 in virtual space 50 set with respect to the scanner position and determines that the three-dimensional data including color information on the closest color to the specific color is true three-dimensional data. In the foregoing example, if the N-th three-dimensional data is applied to "first three-dimensional data," the N+1-th three-dimensional data is applied to "second three-dimensional data," and if the N-th three-dimensional data is applied to "second three-dimensional data," the N+1-th three-dimensional data is applied to "first three-dimensional data."

If data processing apparatus 1 determines that three-dimensional data including color information on the closest color to the specific color is true three-dimensional data among a plurality of three-dimensional data pieces, for example, when scan objects like gums and a finger in relatively close colors are compared with each other, it may be difficult to verify three-dimensional data. However, even if three-dimensional data cannot be verified on the basis of colors, in combination with another data verification that compares the detected positions of the three-dimensional data, data processing apparatus 1 can verify the three-dimensional data on the basis of the detected positions without verifying the three-dimensional data on the basis of colors.

Specifically, when the N-th three-dimensional data and the N+1-th three-dimensional data are both present in the same virtual space, even if the N-th three-dimensional data includes the position of a tooth and the N+1-th three-dimensional data includes the position of a finger or a tongue, the three-dimensional data including a finger or a tongue is verified as true data in the processing that determines that the N+1-th three-dimensional data is true data (the processing illustrated in FIG. 7). In this respect, in the processing illustrated in FIG. 16, even if the N-th three-dimensional data includes the position of a tooth and the N+1-th three-dimensional data includes the position of a finger or a tongue, color information included in the N-th three-dimensional data and color information included in the N+1-th three-dimensional data are compared with each other, thereby determining that the N-th three-dimensional data including color information on the closest color to the specific color is true three-dimensional data. Thus, with this processing, data processing apparatus 1 can determine that three-dimensional data including a finger or a tongue is not true three-dimensional data.

(Virtual Space)

Data processing apparatus 1 according to the present embodiment generates cylindrical virtual space 50 with the central axis located on optical axis L of three-dimensional scanner 2. However, data processing apparatus 1 according to the modification is not limited to cylindrical virtual space 50 and may generate virtual space 50 in other shapes. For example, data processing apparatus 1 may generate virtual space 50 like a polygonal column (e.g., a quadrangular prism) with the central axis located at optical axis L of three-dimensional scanner 2.

(Data Set Verification)

Data processing apparatus 1 according to the present embodiment generates meshes by connecting a plurality of three-dimensional data pieces in a predetermined range via straight lines through mesh generation, sets a group of generated meshes as a data set, and verifies the data set through data set verification. Data processing apparatus 1 according to the modification may verify a data set without generating meshes.

For example, data processing apparatus 1 may classify three-dimensional data by containing a plurality of three-dimensional point cloud data pieces, which are located in a predetermined range, in a common data set without connecting the data pieces via straight lines. In other words, a plurality of three-dimensional point cloud data pieces located in the predetermined range are contained in the common data set without being connected to one another (without generating meshes). Moreover, data processing apparatus 1 may set a data set with the largest data amount (three-dimensional point cloud data) as a true data set (three-dimensional point cloud data) among a plurality of data sets (three-dimensional point cloud data).

Data processing apparatus 1 according to the present embodiment sets a data set with the largest data amount as a true data set among a plurality of data sets. Data processing apparatus 1 according to the modification may set a data set with a predetermined data amount or more as a true data set among a plurality of data sets and generate two-dimensional image data corresponding to a two-dimensional image viewed from any viewpoint, on the basis of the data set with the predetermined data amount or more.

(Verification Index)

As shown in FIG. 10, data processing apparatus 1 according to the present embodiment sets the deletion flag as an index of falsehood for three-dimensional data not verified as true three-dimensional data through data verification. However, data processing apparatus 1 according to the modification may associate three-dimensional data verified as true data through data verification with an index of truth.

As shown in FIG. 10, data processing apparatus 1 according to the present embodiment stores three-dimensional data verified as true three-dimensional data through data verification and three-dimensional data verified as false three-dimensional data in storage device 12 (storage unit 1103) and discriminates between the true three-dimensional data and the false three-dimensional data by using the deletion flag. However, data processing apparatus 1 according to the modification may temporarily store acquired three-dimensional data in storage device 12 and then delete three-dimensional data verified as false three-dimensional data through data verification. In one embodiment, data processing apparatus 1 according to the modification may store only three-dimensional data verified as true three-dimensional data through data verification in storage device 12 among acquired three-dimensional data.

(Three-Dimensional Scanner)

Three-dimensional scanner 2 according to the present embodiment is configured such that the user can move probe 22 held with a hand. However, in three-dimensional scanner 2 according to the modification, housing 21 and probe 22 may be fixed.

Three-dimensional scanner 2 is not limited to a device that uses the reflection of an optical axis to acquire three-dimensional data on points representing the surface of a scan object. For example, three-dimensional scanner 2 may be a device that uses a laser beam to acquire three-dimensional data on points representing the surface of a scan object.

Moreover, three-dimensional scanner 2 may be a device like a CT (Computed Tomography) scanner or an X-ray apparatus that acquires voxel data or volume data including position information on points constituting the inside of a scan object as well as the surface of the scan object.

It should be understood that the disclosed embodiment is merely exemplary and is not restrictive in all the aspects. The scope of the present disclosure is not indicated by the foregoing description but the claims. The scope of the present disclosure is intended to include meanings equivalent to the claims and all changes in the scope. The configuration illustrated in the present embodiment and the configuration illustrated in the modification may be combined as appropriate.

Although the present disclosure has been described and illustrated in detail, it is clearly understood that the same is by way of illustration and example only and is not to be taken by way of limitation, the scope of the present disclosure being interpreted by the terms of the appended claims.

What is claimed is:

1. A data processing apparatus that processes three-dimensional data including a position of each point of a point group representing at least a surface of an object, the three-dimensional data being acquired by a three-dimensional scanner,
    the data processing apparatus comprising:
        a scanner interface to which the three-dimensional data acquired by the three-dimensional scanner is input; and
        processing circuitry configured to conduct a verification of first three-dimensional data input from the scanner interface and second three-dimensional data input from the scanner interface by comparing the first three-dimensional data and the second three-dimensional data in a virtual space set with respect to a position of the three-dimensional scanner, wherein
    the verification includes:
        determining that three-dimensional data input later, from the scanner interface, is true three-dimensional data in the comparison between the first three-dimensional data and the second three-dimensional data;
        determining that three-dimensional data including a position of a farthest point from the position of the three-dimensional scanner is true three-dimensional data in the comparison between the first three-dimensional data and the second three-dimensional data;
        determining that three-dimensional data including a position of a closest point to the position of the three-dimensional scanner is false three-dimensional data in the comparison between the first three-dimensional data and the second three-dimensional data; or
        determining that three-dimensional data including color information on a closest color to a specific color is true three-dimensional data in the comparison between the first three-dimensional data and the second three-dimensional data.

2. The data processing apparatus according to claim 1, wherein the three-dimensional scanner acquires the three-dimensional data by using an optical axis, and the virtual space is shaped like a cylinder or a polygonal column with a central axis located on the optical axis of the three-dimensional scanner.

3. The data processing apparatus according to claim 1, wherein the verification includes at least one of associating an index of falsehood with false three-dimensional data, associating an index of truth with true three-dimensional data, deleting the false three-dimensional data stored in a storage device, and storing the true three-dimensional data in the storage device.

4. The data processing apparatus according to claim 1, wherein the processing circuitry is further configured to generate a data set by using a plurality of three-dimensional data pieces located in a predetermined range from among a plurality of three-dimensional data pieces acquired by the three-dimensional scanner.

5. The data processing apparatus according to claim 4, wherein when a plurality of data sets are generated, the processing circuitry is further configured to set a data set with a largest data amount as a true data set among the plurality of data sets.

6. The data processing apparatus according to claim 5, wherein the processing circuitry is configured to set the true data set when a predetermined condition is satisfied, and
    the predetermined condition includes at least one of a first condition that a data amount of the three-dimensional data input from the scanner interface exceeds a predetermined amount and a second condition that a time for inputting the three-dimensional data from the scanner interface exceeds a predetermined time.

7. The data processing apparatus according to claim 4, wherein when a plurality of data sets are generated, the processing circuitry is further configured to set a data set with at least a predetermined data amount as a true data set among the plurality of data sets.

8. The data processing apparatus according to claim 1, wherein the three-dimensional scanner is a hand-held handpiece that acquires three-dimensional data including the position of each point of the point group representing the surface of the object, the three-dimensional data being acquired by scanning the object in an oral cavity.

9. A data processing method for processing three-dimensional data including a position of each point of a point group representing at least a surface of an object, the three-dimensional data being acquired by a three-dimensional scanner,
    the data processing method comprising:
        receiving, via processing circuitry, the three-dimensional data acquired by the three-dimensional scanner; and
        conducting, via the processing circuitry, a verification of first three-dimensional data received by the processing circuitry and second three-dimensional data received by the processing circuitry by comparing the first three-dimensional data and the second three-dimensional data in a virtual space set with respect to a position of the three-dimensional scanner, wherein
    the verification includes:
        determining that three-dimensional data input later, from the scanner interface, is true three-dimensional data in the comparison between the first three-dimensional data and the second three-dimensional data;
        determining that three-dimensional data including a position of a farthest point from the position of the three-dimensional scanner is true three-dimensional data in the comparison between the first three-dimensional data and the second three-dimensional data; or determining that three-dimensional data including color information on a closest color to a specific color is true three-dimensional data in the comparison between the first three-dimensional data and the second three-dimensional data.

10. A data processing system comprising:

a three-dimensional scanner that acquires three-dimensional data including a position of each point of a point group representing at least a surface of an object by scanning the object in an oral cavity; and a data processing apparatus configured to process the three-dimensional data acquired by the three-dimensional scanner, the data processing apparatus including:

a scanner interface to which the three-dimensional data acquired by the three-dimensional scanner is input; and processing circuitry configured to conduct a verification of first three-dimensional data input from the scanner interface and second three-dimensional data input from the scanner interface by comparing the first three-dimensional data and the second three-dimensional data in a virtual space set with respect to a position of the three-dimensional scanner, wherein the verification includes:

determining that three-dimensional data input later, from the scanner interface, is true three-dimensional data in the comparison between the first three-dimensional data and the second three-dimensional data;

determining that the three-dimensional data including a position of a farthest point from the position of the three-dimensional scanner is true three-dimensional data in the comparison between the first three-dimensional data and the second three-dimensional data; or determining that three-dimensional data including color information on a closest color to a specific color is true three-dimensional data in the comparison between the first three-dimensional data and the second three-dimensional data.

* * * * *